(12) United States Patent
Sakurai et al.

(10) Patent No.: US 8,207,144 B2
(45) Date of Patent: *Jun. 26, 2012

(54) SODIUM SALT OF DISACCHARIDE COMPOUND, PRODUCTION METHOD AND USE OF SAME

(75) Inventors: Shin Sakurai, Choshi (JP); Ken Furukawa, Kashima (JP); Kimihiro Matsuo, Kamisu (JP); Kenichi Tagami, Kamisu (JP)

(73) Assignee: Eisai R & D Management Co., Ltd., Tokyo (JP)

( * ) Notice: Subject to any disclaimer, the term of this patent is extended or adjusted under 35 U.S.C. 154(b) by 790 days.

This patent is subject to a terminal disclaimer.

(21) Appl. No.: 11/984,770

(22) Filed: Nov. 21, 2007

(65) Prior Publication Data

US 2008/0227991 A1 Sep. 18, 2008

Related U.S. Application Data

(60) Provisional application No. 60/860,483, filed on Nov. 22, 2006.

(51) Int. Cl.
*A61K 31/7016* (2006.01)
*C07H 11/04* (2006.01)

(52) U.S. Cl. .......................................... 514/53
(58) Field of Classification Search .................. None
See application file for complete search history.

(56) References Cited

U.S. PATENT DOCUMENTS

| | | |
|---|---|---|
| 6,184,366 B1 * | 2/2001 | Christ et al. ................. 536/17.2 |
| 2002/0019521 A1 | 2/2002 | Orr et al. |
| 2006/0160999 A1 | 7/2006 | Fan |

FOREIGN PATENT DOCUMENTS

| | | |
|---|---|---|
| JP | 2006-518394 A | 8/2006 |
| WO | WO-96/39411 A1 | 12/1996 |
| WO | WO-2004/071465 A2 | 8/2004 |
| WO | WO-2004/074303 A2 | 9/2004 |

OTHER PUBLICATIONS

Berge, S. M. et al., Journal of Pharmaceutical Sciences "Pharmaceutical Salts", vol. 66, issue 1, Jan. 1977.*
McMahon et al.; Journal of Pharmacology and Experimental Therapeutics, 2004, vol. 308, No. 1, pp. 175-181.
Yun-peng Zhu et al., *Preparation and Surface-Active Properties of New Amphipathic Compounds with Two Phosphate Groups and Two Long-Chain Alkyl Groups*, 68(4) JAOCS 268-271 (Apr. 1991).
Office Action mailed Oct. 19, 2011, issued in U.S. Appl. No. 12/516,082.

* cited by examiner

*Primary Examiner* — Shaojia Anna Jiang
*Assistant Examiner* — Bahar Schmidtmann

(74) *Attorney, Agent, or Firm* — Buchanan Ingersoll & Rooney PC

(57) ABSTRACT

The present invention relates to a composition comprising a plurality of sodium salts represented by the formula (I):

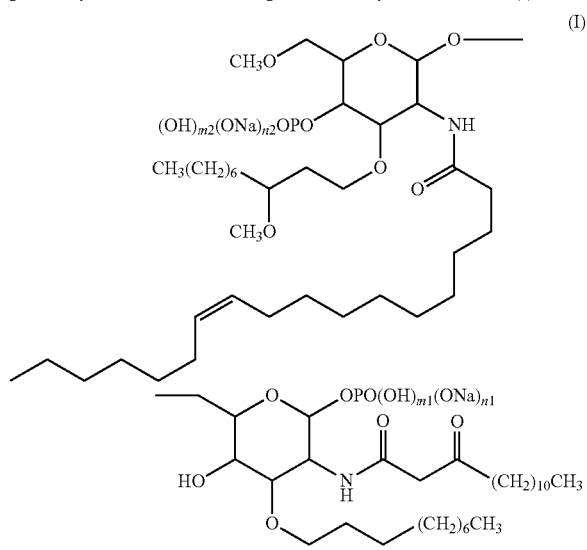

wherein, $m_1$, $n_1$, $m_2$ and $n_2$ respectively and independently represent a positive number between 0 and 2, provided that $m_1+n_1=2$, $m_2+n_2=2$, $0<m_1+m_2<4$ and $0<n_1+n_2<4$,
and a method for producing the same, and
a method for inhibiting the decomposition of a sodium salt represented by general formula (IV):

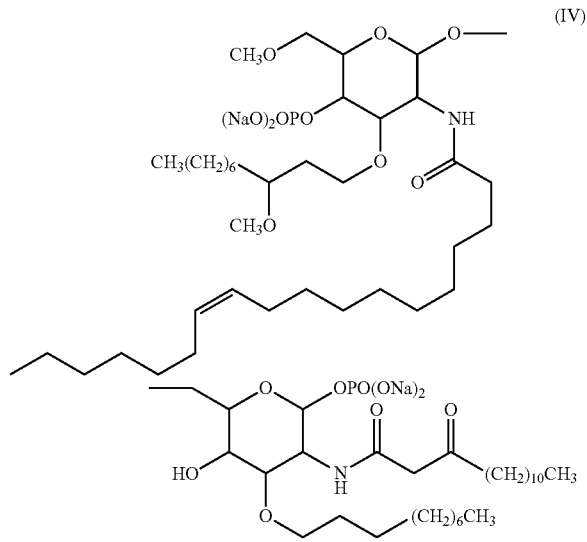

comprising: having the sodium salt represented by general formula (IV) in the presence of the sodium salts represented by formula (I), and according to the present invention the stability over time of the sodium salt represented by general formula (IV) is improved.

6 Claims, 2 Drawing Sheets

SODIUM SALT OF DISACCHARIDE COMPOUND, PRODUCTION METHOD AND USE OF SAME

The present application claims priority on Japanese Patent Application No. 2006-315020, filed on Nov. 22, 2006, and U.S. Patent Application No. 60/860,483, filed on Nov. 22, 2006, the contents of which are incorporated herein by reference.

BACKGROUND OF THE INVENTION

1. Field of the Invention

The present invention relates to a sodium salt of a disaccharide compound represented by the formula indicated below.

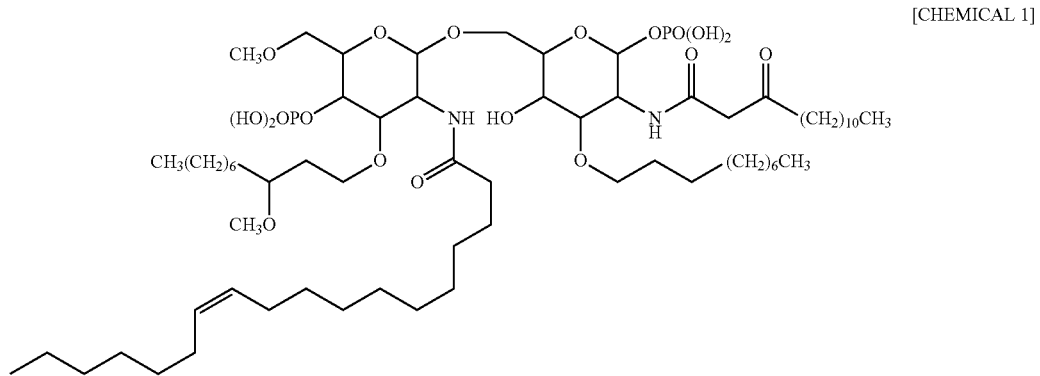

[CHEMICAL 1]

2. Description of the Related Art

A compound represented by the above formula, and a tetrasodium salt thereof, is known to have superior effects for the prevention and treatment of gram-negative bacteremias, particularly endotoxic shock, having a high mortality rate caused by lipopolysaccharides (LPS) or endotoxins present in the outer membrane of gram-negative bacteria. In addition, it has also been confirmed to have superior anti-endotoxin activity in humans (Non-Patent Document 1). And, it is also known to have antagonistic activity against toll-like receptor 4 (TLR-4), which is one of the receptors that recognize bacterial cellular components (Patent Documents 1 and 2). On the basis of these actions, the aforementioned compound and tetrasodium salt thereof have been reported to be particularly useful as preventives or therapeutics for septicemia, endotoxemia or improving prognosis following coronary artery bypass surgery (Patent Documents 2 and 3).

[Patent Document 1] International Publication No. WO 2004/071465
[Patent Document 2] International Publication No. WO 96/39411
[Patent Document 3] International Publication No. WO 2004/074303
[Non-Patent Document 1] Lynn, et al., J. Pharmacol. Exp. Ther., 308(1): 175-181, 2004

SUMMARY OF THE INVENTION

However, tetrasodium salts of the aforementioned compound have recently been found to slightly decompose during storage and form trace amounts of impurities over time depending on the storage conditions. From the viewpoint of safety for use as a pharmaceutical, decomposition of sodium salts of the aforementioned compound over time should be avoided as much as possible.

Therefore, an object of the present invention is to provide a pharmaceutical that inhibits decomposition of sodium salts of the compound represented by the aforementioned formula over time, reduces the formation of impurities and has superior safety.

The aforementioned object is achieved by a composition comprising a plurality of sodium salts represented by formula (I):

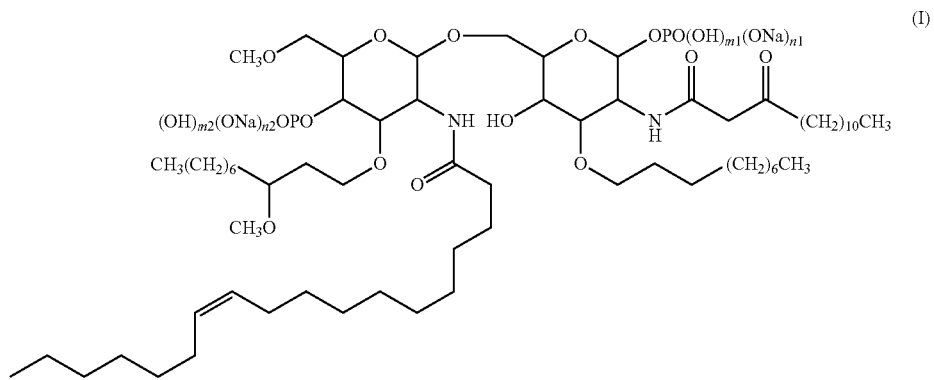

wherein, $m_1$, $n_1$, $m_2$ and $n_2$ respectively and independently represent a positive number between 0 and 2, provided that $m_1+n_1=2$, $m_2+n_2=2$, $0<m_1+m_2<4$ and $0<n_1+n_2<4$.

In the aforementioned formula (I), $3 \leq n_1+n_2<4$ is preferable, and $3.5 \leq n_1+n_2 \leq 3.8$ is more preferable.

In addition, the sodium content of the sodium salts represented by the aforementioned formula (I) is preferably 5.0 to less than 6.5% by weight, more preferably 5.7 to 6.3% by weight.

The composition comprising a plurality of sodium salts represented by average formula (I) can be obtained by incompletely neutralizing a compound represented by general formula (II):

[CHEMICAL 3]

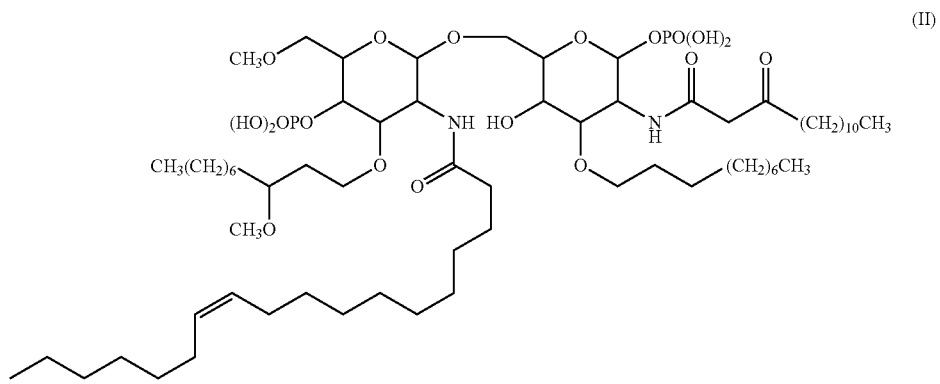

with a sodium-containing base.

In addition, the object of the present invention can also be achieved by a sodium salt represented by general formula (III):

[CHEMICAL 4]

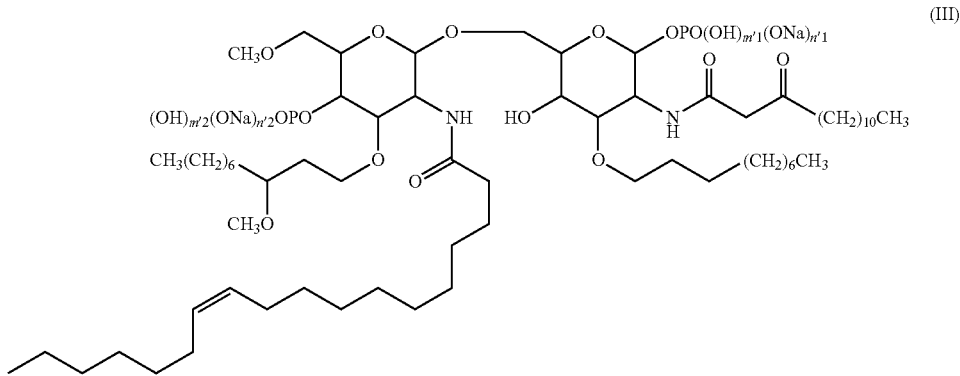

(III)

(wherein, $m'_1$, $n'_1$, $m'_2$ and $n'_2$ respectively and independently represent an integer of 0 or 2 or less, provided that $m'_1+n'_1=2$, $m'_2+n'_2=2$, $0<m'_1+m'_2<4$ and $0<n'_1+n'_2<4$).

More specifically, decomposition of a sodium salt represented by general formula (IV):

[CHEMICAL 5]

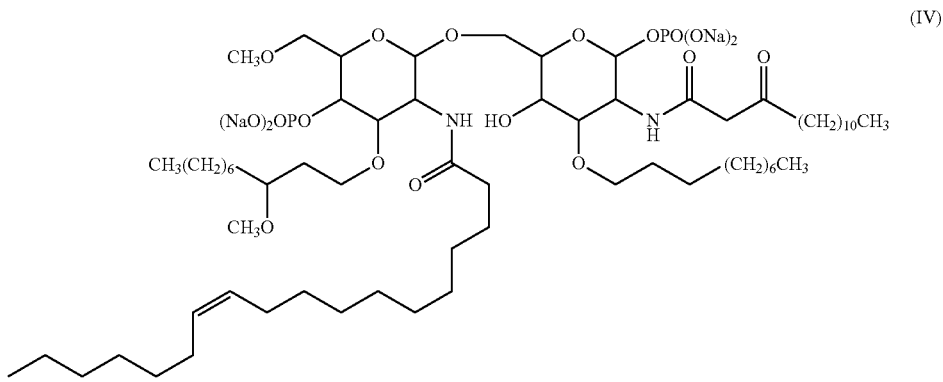

(IV)

is inhibited and the formation of impurities within said salt is inhibited by having the sodium salt represented by general formula (IV) in the presence of the sodium salt represented by general formula (III).

Thus, the object of the present invention is achieved by storing the sodium salt represented by the aforementioned general formula (IV) together with the sodium salt represented by general formula (III).

Since decomposition of the sodium salt of the present invention represented by average formula (I) over time is inhibited as much as possible and is highly stable, it has superior safety as a pharmaceutical. The case in which $3 \leq n_1+n_2<4$ in average formula (I), and particularly the case in which $3.5 \leq n_1+n_2 \leq 3.8$, or the case in which the sodium content is 5.0 to less than 6.5% by weight, and particularly 5.7 to 6.3% by weight, is superior.

Since a method for producing the sodium salt represented by average formula (I) of the present invention does not use substances harmful to the human body and does not involve a complicated process, it is superior as a pharmaceutical production method.

In addition, since the sodium salt represented by general formula (III) of the present invention inhibits decomposition of the sodium salt represented by general formula (IV) over time and reduces the formation of impurities, the sodium salt represented by general formula (IV) can be stored over a long period of time.

Since a salt represented by average formula (I) of the present invention is useful as a preventive or therapeutic for septicemia, endotoxemia or improving prognosis following coronary artery bypass surgery, and has superior stability over time in particular, it can be used as an active ingredient of preparations capable of being stored for an extended period of time.

In addition, since a salt represented by general formula (III) of the present invention is able to improve the stability over time of a salt represented by general formula (IV) that is similarly useful as a preventive or therapeutic for septicemia, endotoxemia or improving prognosis following coronary artery bypass surgery, it can be used as a production raw material of a pharmaceutical capable of being stored for an extended period of time by using in combination with the salt represented by general formula (IV).

DESCRIPTION OF THE PREFERRED EMBODIMENTS

Figure 1:
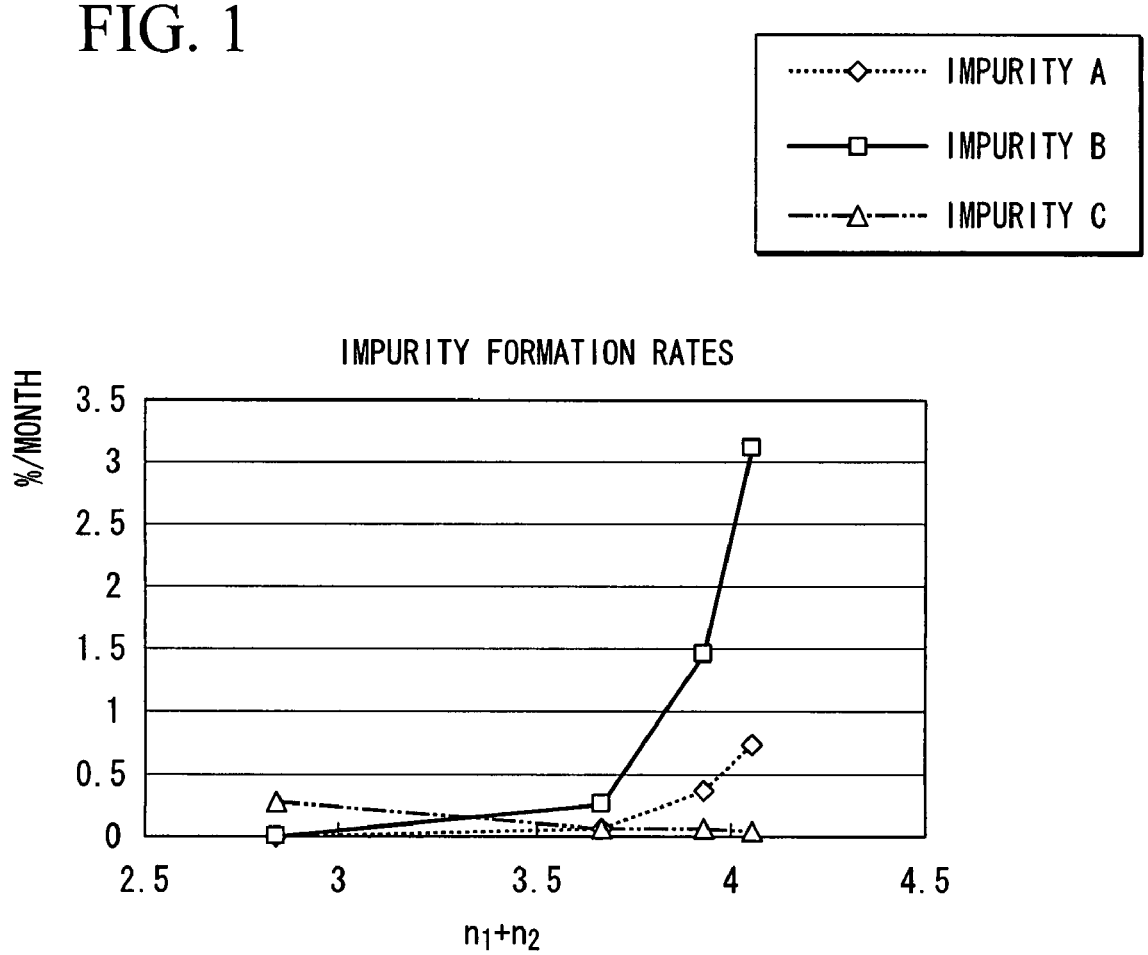
FIG. 1 is a first drawing showing impurity formation rates of Examples 2 to 4 and Comparative Example 1; and, FIG. 2 is a second drawing showing impurity formation rates of Examples 2 to 4 and Comparative Example 1.

A compound represented by general formula (II) and a compound represented by general formula (IV) in the form of a tetrasodium salt thereof, as related to the present invention, can be synthesized by an arbitrary known method.

A compound represented by general formula (IV) can be synthesized by, for example, going through the following steps as described in WO 96/39411 (Patent Document 2).

[CHEMICAL 6]

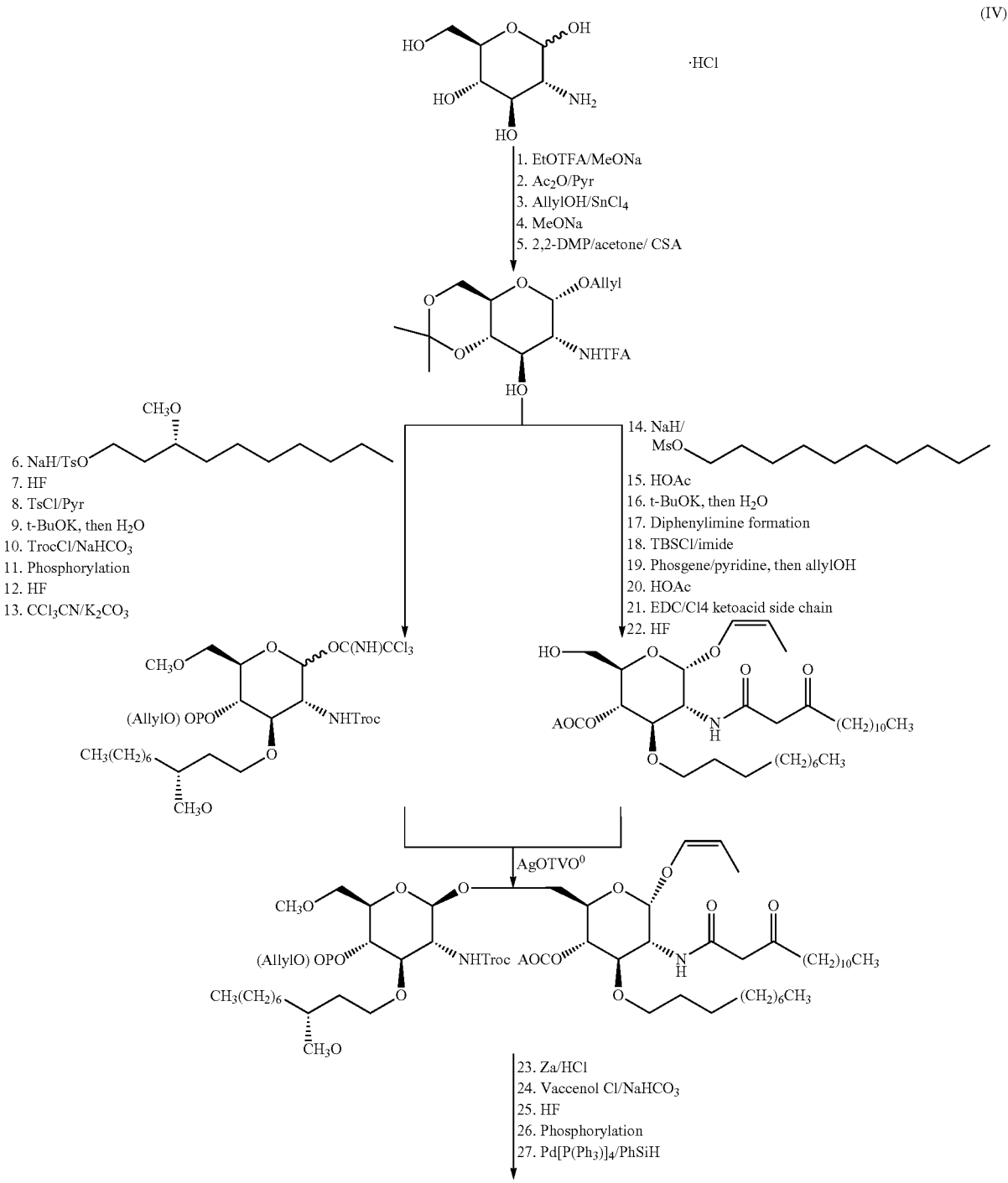

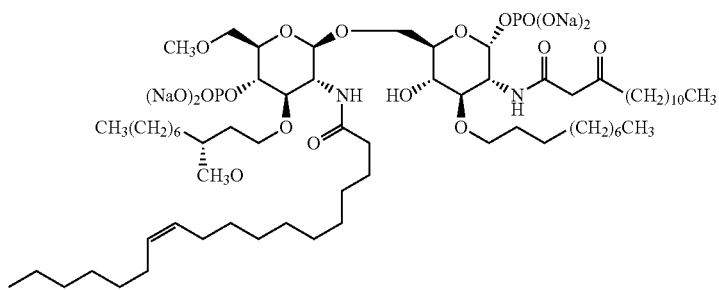

In addition, compounds represented by general formula (II) and general formula (IV) can also be synthesized by going through the following reaction scheme 1, in which two acyl side chains are introduced in advance into a monosaccharide followed by the bonding thereof, and by going through a reaction scheme 2, in which the compound obtained in reaction scheme 1 is phosphorylated, as described in, for example, WO 2004/074303 (Patent Document 3).

Reaction Scheme 1

[CHEMICAL 7]

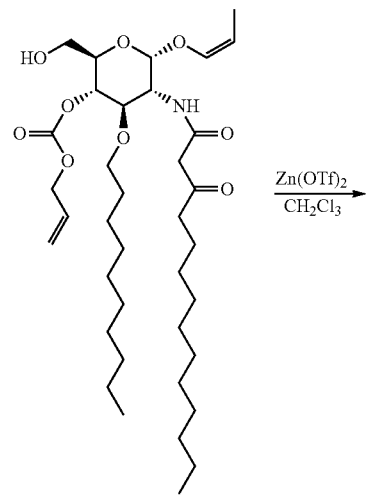

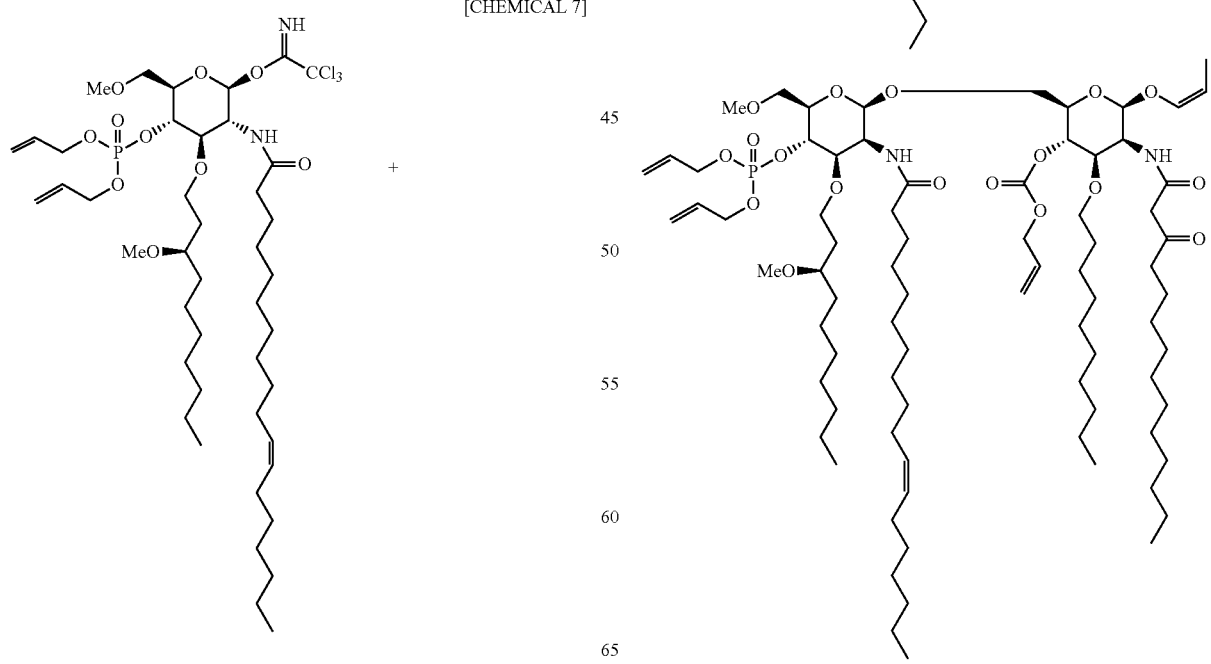

Reaction Scheme 2
[CHEMICAL 8]
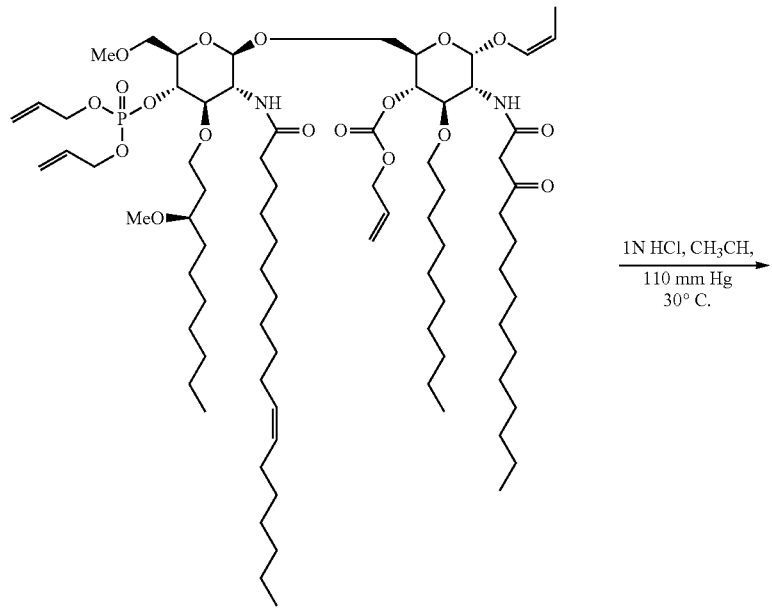
1N HCl, CH₃CH,
110 mm Hg
30° C.
1) Bis(allyloxy)diisopropyl-
   aminophosohine, tetrazole
2) Oxone -continued
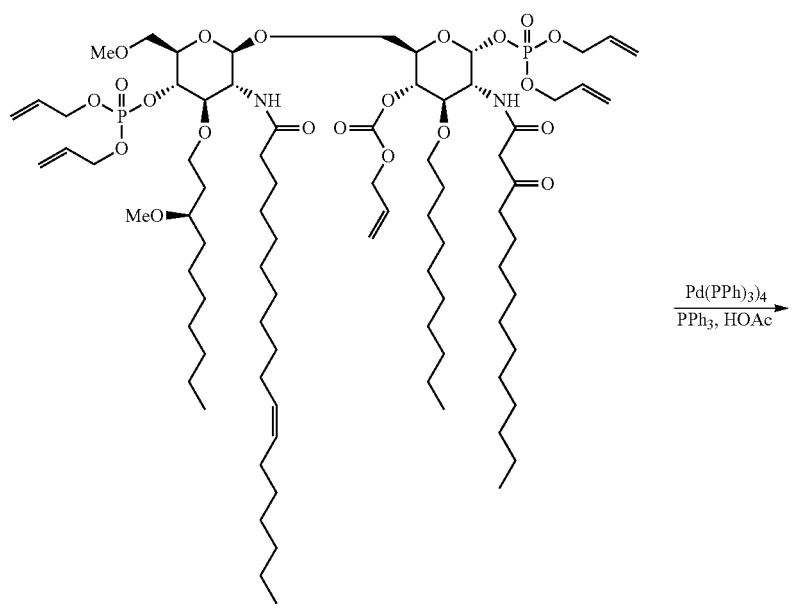
Pd(PPh₃)₄
PPh₃, HOAc
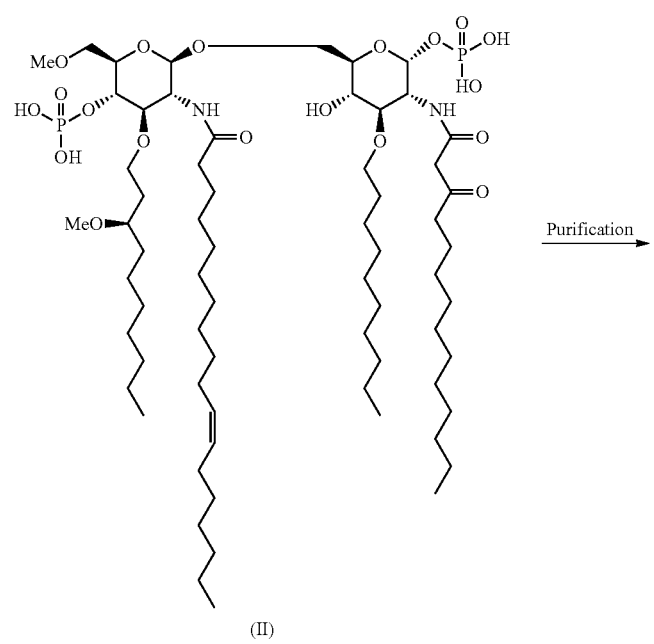
(II)
Purification

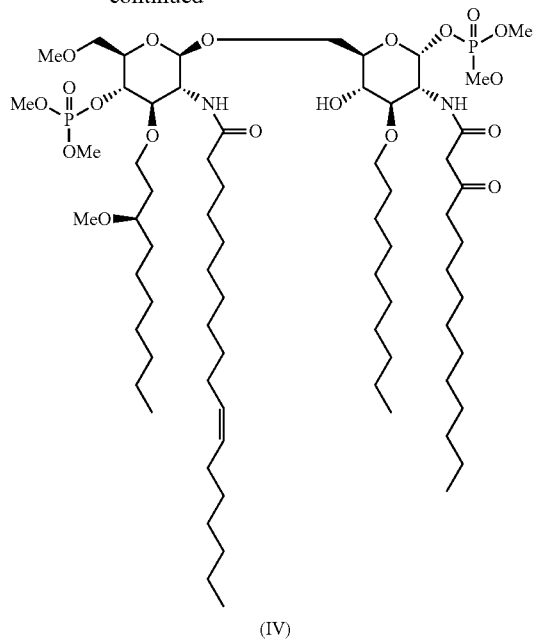

(IV)

However, the method described in WO 96/39411 (Patent Document 2) has problems in terms of production efficiency due to the large number of steps. In addition, although the method of WO 2004/074303 (Patent Document 3) has considerably fewer synthesis steps, it uses reagents that are toxic to the human body and reagents that are explosive, thereby leaving room for improvement in terms of safety and procedural ease.

Thus, it is preferable that the compounds represented by general formulas (II) and (IV) are produced by the following method having few synthesis steps without using reagents that are toxic to the human body or explosive.

[CHEMICAL 9]

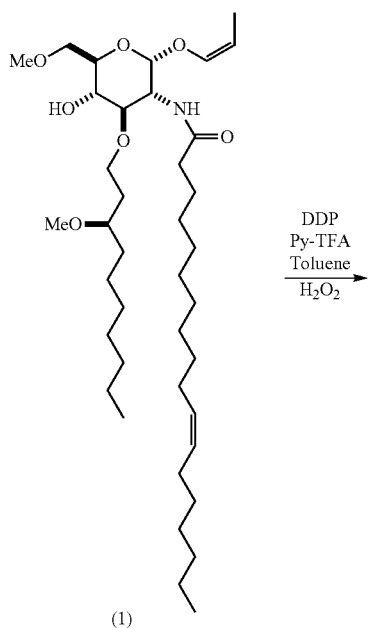

(1)

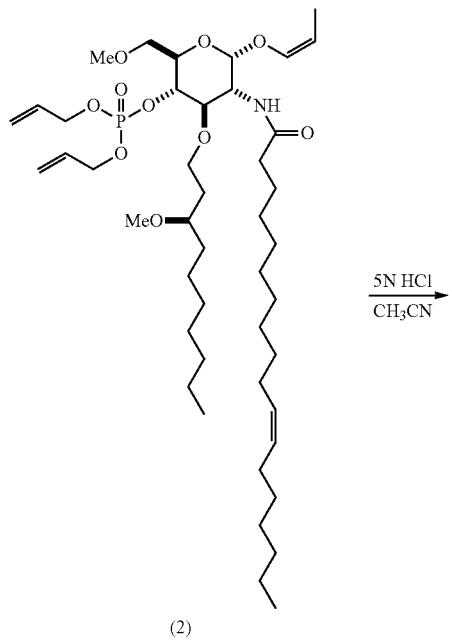

(2)

DDP: Dially-N,N-diisopropylphosphoramidate
Py: Pyridine
TFA: Trifluoroacetic acid

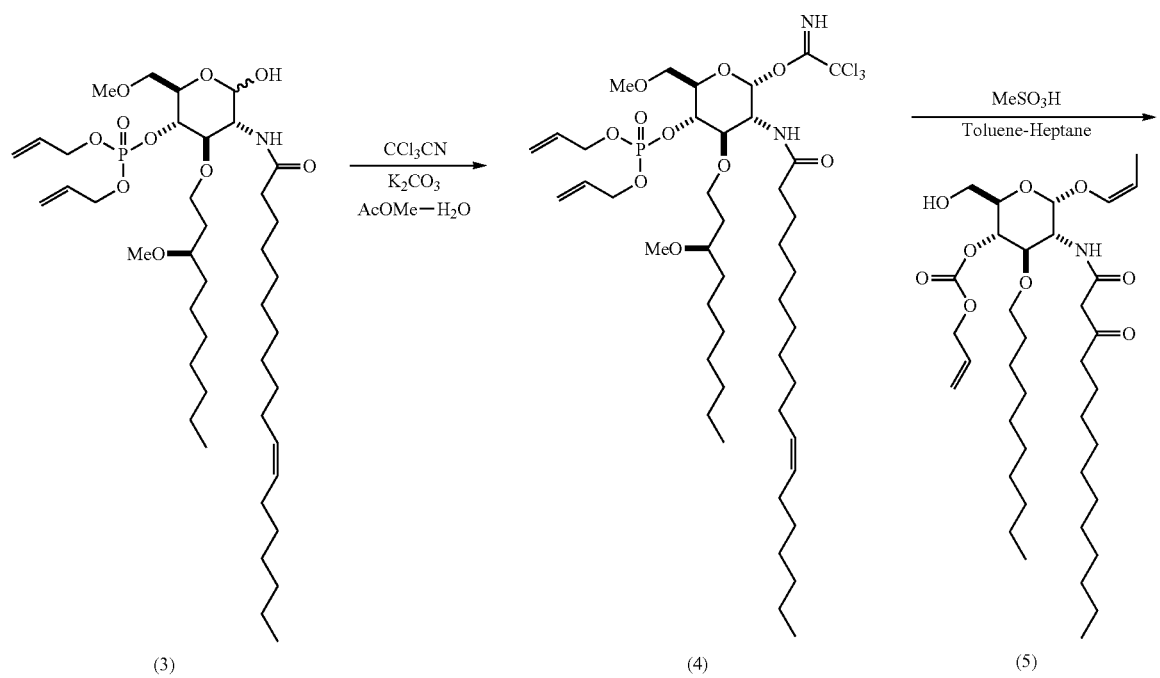
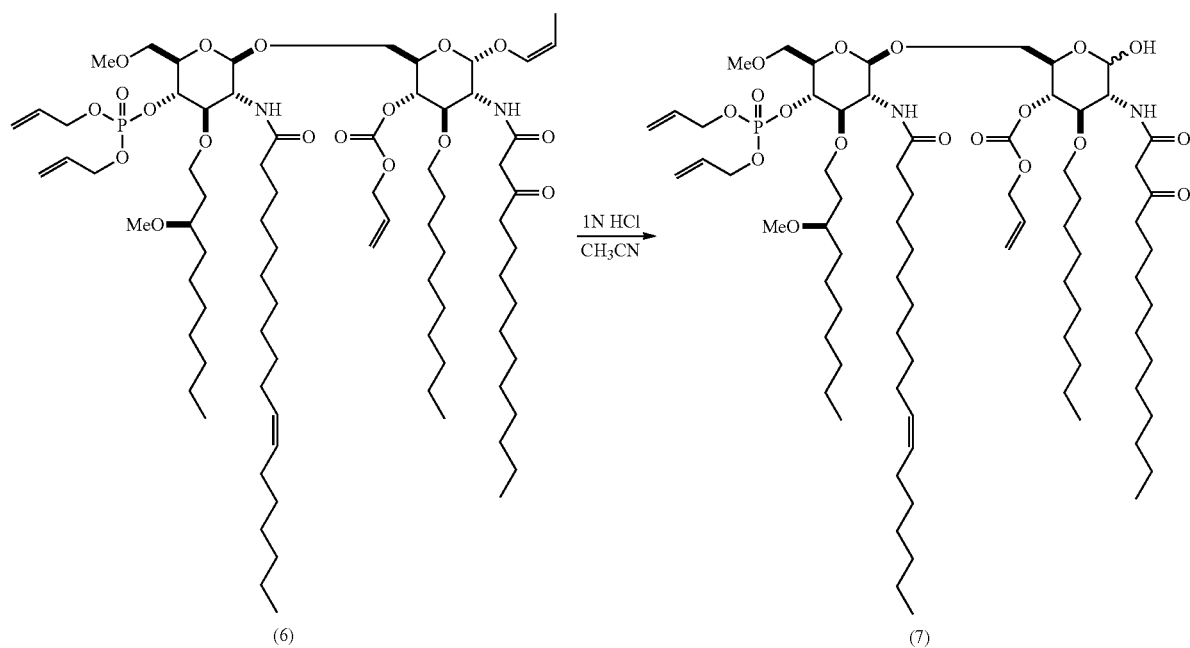

[CHEMICAL 11]

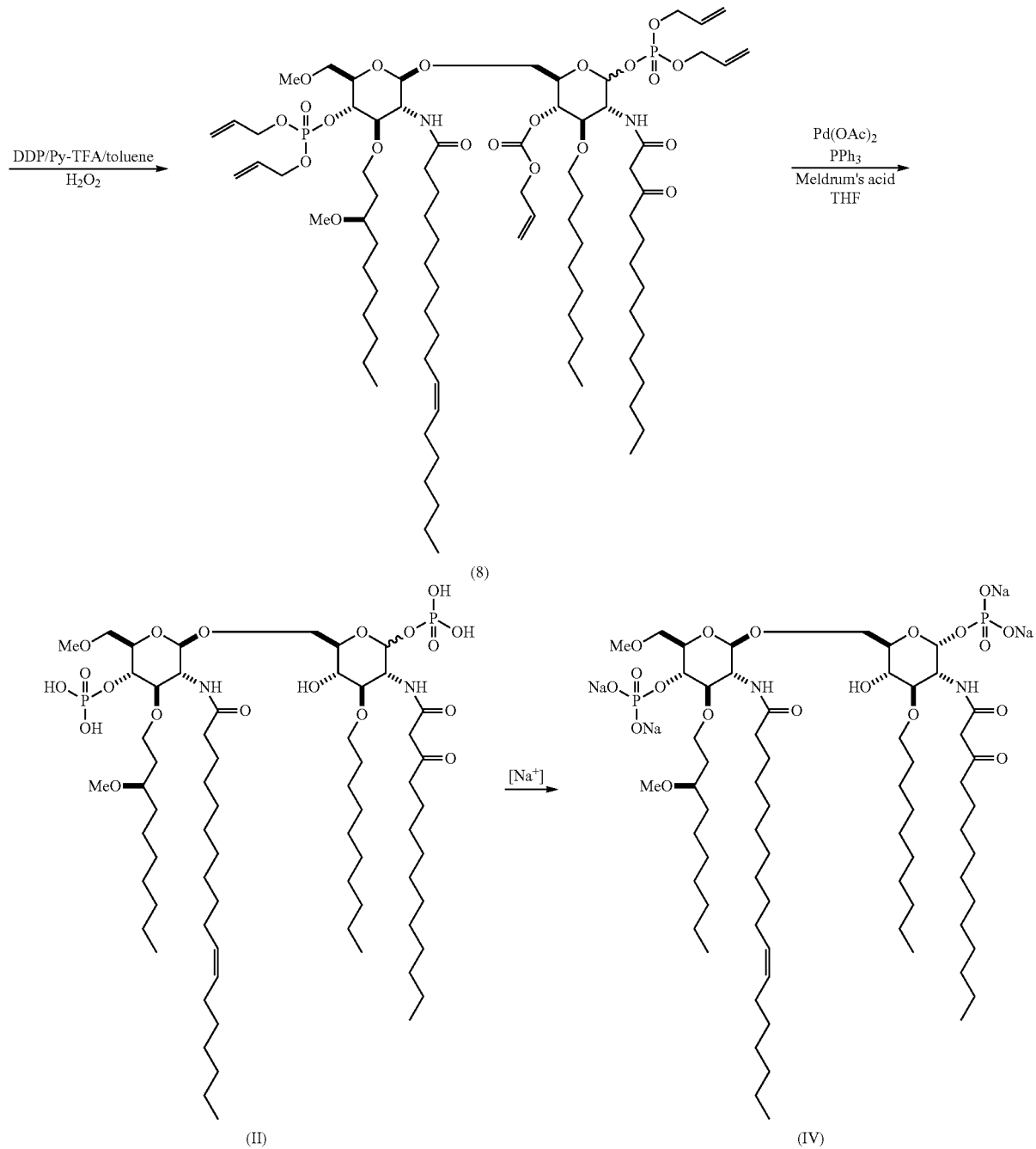

A first step of the aforementioned production method consists of introducing a phosphite group into a compound of formula (1) followed by going through an oxidation reaction to obtain a compound of formula (2). There are no particular limitations on the solvent used in the present step, and an inert solvent that does not easily react with the reactants is preferable, examples of which include ethers such as tetrahydrofuran, diethyl ether, diisopropyl ether, dioxane or dimethoxyethane; halogenated hydrocarbons such as chloroform, carbon tetrachloride or 1,2-dichloroethane; hydrocarbons such as hexane or heptane; aromatic hydrocarbons such as benzene or toluene; acetic acid esters such as ethyl acetate or methyl acetate; amides such as N,N-dimethylformamide, N-methyl-2-piperidone or hexamethyl phosphorylamide; sulfoxides such as dimethylsulfoxide and mixtures thereof, with aromatic hydrocarbons being preferable and toluene, for example, being particularly preferable.

In the present step, the reaction proceeds under mild conditions by carrying out the reaction in the presence of pyridine and trifluoroacetic acid. Although the pyridine and trifluoroacetic acid used in the present step can be used in an equal amount to an excess amount with respect to the compound of formula (1), in consideration of ensuring that the reaction proceeds smoothly, purification treatment and the like, they are preferably used at 1.0 to 3.0 equivalents and 1.0 to 3.0 equivalents, respectively, and preferably at 1.0 to 2.0 equivalents and 1.0 to 2.0 equivalents, respectively.

The present step is composed of a total of two steps consisting of a step for introducing a phosphite group and an oxidation step, and although diallyl-N,N-diisopropyl-phosphoramidate used in the step for introducing a phosphite group can be used in an equal amount to an excess amount with respect to the compound of formula (1), it is preferably used at 1.0 to 2.0 equivalents. The reaction time of the phosphite group introduction step is 0.5 to 4 hours and preferably 1 to 2 hours. The reaction temperature is −78° C. to room temperature and preferably −40 to 0° C. Although examples of the oxidant used in the oxidation step include hydrogen peroxide, m-chloroperbenzoic acid and oxone, hydrogen peroxide is most preferable. Although hydrogen peroxide can be used in an equal amount to an excess amount with respect to the compound of formula (1), it is preferably used at 1.0 to 3.0 equivalents. The reaction time of the oxidation step is 0.5 to 6 hours and preferably 1 to 4 hours. The reaction temperature is preferably −50 to 0° C.

The second step of the aforementioned production method consists of selectively deprotecting a 1-propenyl group from the compound of formula (2) by acid hydrolysis to produce the compound of formula (3). There are no particular limitations on the solvent used in the present step, and an inert solvent that does not easily react with the reactants is preferable, examples of which include alcohols such as methanol, ethanol, isopropanol or tert-butanol; ethers such as tetrahydrofuran, diethyl ether, diisopropyl ether, dioxane, dimethoxyethane, diethoxyethane or diglyme; halogenated hydrocarbons such as chloroform, carbon tetrachloride or 1,2-dichloroethane; hydrocarbons such as hexane or heptane; aromatic hydrocarbons such as benzene or toluene; nitriles such as acetonitrile; amides such as N,N-dimethylformamide, N,N-dimethylacetoamide, N-methyl-2-piperidone or hexamethyl phosphorylamide; and sulfoxides such as dimethylsulfoxide, with nitriles such as acetonitrile being preferable.

Examples of acids used in the present step include ordinary organic acids and inorganic acids. Examples of organic acids that can be used include carboxylic acids such as acetic acid, trifluoroacetic acid, propionic acid or benzoic acid; dicarboxylic acids such as oxalic acid; and organic sulfonic acids such as methanesulfonic acid, tosic acid or trifluoromethanesulfonic acid, while examples of inorganic acids include phosphoric acid, hydrochloric acid, sulfuric acid and nitric acid, with inorganic acids such as hydrochloric acid or sulfuric acid being preferable.

Although the acid used in the present step can be used in a catalytic amount to an excess amount with respect to the compound of formula (2), in consideration of ensuring that the reaction proceeds smoothly, purification treatment and the like, it is preferably used at 0.01 to 1.5 equivalents and particularly preferably at 0.1 to 1.0 equivalent.

The reaction time is 0.5 to 12 hours and preferably 1 to 6 hours. The reaction temperature is 0° C. to the heating reflux temperature, and preferably 10 to 60° C.

Furthermore, effects such as improving purity are obtained for the resulting compound of formula (3) by obtaining crystals under optimum conditions.

The third step of the aforementioned production method consists of introducing a trichloroacetoimidate group as a leaving group into the compound of formula (3) in the presence of base to produce the compound of formula (4). Although the trichloroacetonitrile used in the present step can be used in an equal amount to an excess amount with respect to the compound of formula (3), in consideration of ensuring that the reaction proceeds smoothly, purification treatment and the like, it is preferably used at 1.0 to 10.0 equivalents and particularly preferably at 2.0 to 5.0 equivalents.

Examples of solvents used in the present step include ethers such as tetrahydrofuran, diethyl ether, diisopropyl ether, dioxane or dimethoxyethane; halogenated hydrocarbons such as chloroform, carbon tetrachloride or 1,2-dichloroethane; acetic acid esters such as methyl acetate or ethyl acetate, water and mixtures thereof, with mixtures of water and acetic acid esters such as methyl acetate or ethyl acetate being particularly preferable since they allow the reaction to be carried out with favorable reproducibility.

The mixing ratio of acetic acid ester and water used as solvent is 1 to 10% (volume/volume), and preferably 2 to 5%, as the ratio of water.

Examples of bases used in the present step include carbonates such as sodium carbonate, potassium carbonate or cesium carbonate; bicarbonates such as sodium bicarbonate; and alkaline metal alkoxides such as sodium methoxide or potassium tert-butoxide, with carbonates such as potassium carbonate being preferable.

Although the base used in the present step can be used in an equal amount to an excess amount with respect to the compound of formula (3), in consideration of ensuring that the reaction proceeds smoothly, purification treatment and the like, it is preferably used at 0.5 to 3.0 equivalents and particularly preferably at 1.0 to 1.3 equivalents.

The reaction time is 0.5 to 24 hours and preferably 1 to 5 hours. The reaction temperature is preferably −20° C. to room temperature and particularly preferably −5 to 10° C.

The fourth step of the aforementioned production method consists of forming a glycosyl bond between the compound of formula (4) and the compound of formula (5) to produce the compound of formula (6). The glycosylation reaction is able to proceed in the presence of an acid catalyst. Examples of acid catalysts used in the present step include organic acids and Lewis acids. Preferable examples of organic acids include organic sulfonic acids such as methanesulfonic acid, ethanesulfonic acid, camphorsulfonic acid or p-toluenesulfonic acid, while particularly preferable examples include methanesulfonic acid and ethanesulfonic acid.

A solvent used in the present step is preferably an inert solvent that does not easily react with the reactants, examples of which include ethers such as tetrahydrofuran, diethyl ether, diisopropyl ether, dioxane or dimethoxyethane; halogenated hydrocarbons such as chloroform, carbon tetrachloride or 1,2-dichloroethane; hydrocarbons such as hexane or heptane; aromatic hydrocarbons such as benzene or toluene; and nitrites such as acetonitrile or mixtures thereof. Hydrocarbons such as hexane or heptane, and aromatic hydrocarbons such as benzene or toluene or mixtures thereof are preferable, while mixed solvents of heptane and toluene are particularly preferable. The reaction temperature is 0° C. to the heating reflux temperature, and preferably 10 to 30° C. The reaction time is 1 to 7 days and preferably 8 hours to 3 days.

The fifth step of the aforementioned production method consists of selecting deprotecting a 1-propenyl group from the compound of formula (6) by acid hydrolysis to produce the compound of formula (7). There are no particular limitations on the solvent used in the present step, and an inert solvent that does not easily react with the reactants is preferable, examples of which include alcohols such as methanol, ethanol, isopropanol or tert-butanol; ethers such as tetrahydrofuran, diethyl ether, diisopropyl ether, dioxane, dimethoxyethane, diethoxyethane or diglyme; halogenated hydrocarbons such as chloroform, carbon tetrachloride or 1,2-dichloroethane; hydrocarbons such as hexane or heptane; aromatic hydrocarbons such as benzene or toluene; nitriles such as acetonitrile; amides such as N,N-dimethylformamide, N,N-dimethylacetoamide, N-methyl-2-piperidone or hexamethyl phosphorylamide; and sulfoxides such as dimethylsulfoxide, with nitriles such as acetonitrile being preferable.

Examples of acids used in the present step include ordinary organic acids and inorganic acids. Examples of organic acids that can be used include carboxylic acids such as acetic acid, trifluoroacetic acid, propionic acid or benzoic acid; dicarboxylic acids such as oxalic acid; and organic sulfonic acids such as methanesulfonic acid, tosic acid or trifluoromethanesulfonic acid, while examples of inorganic acids include phosphoric acid, hydrochloric acid, sulfuric acid and nitric acid, with inorganic acids such as hydrochloric acid or sulfuric acid being preferable.

Although the acid used in the present step can be used in a catalytic amount to an excess amount with respect to the compound of formula (6), in consideration of ensuring that the reaction proceeds smoothly, purification treatment and the like, it is preferably used at 0.01 to 1.5 equivalents and particularly preferably at 0.1 to 0.5 equivalents.

The reaction time is 0.5 to 12 hours and preferably 1 to 6 hours. The reaction temperature is 0° C. to the heating reflux temperature, and preferably 10 to 60° C.

Furthermore, effects such as improving yield, improving procedural ease or reducing by-products are obtained by carrying out the reaction and treatment under reduced pressure.

The sixth step of the aforementioned production method consists of introducing phosphorous acid into the compound of formula (7) followed by going through an oxidation reaction to obtain the compound of formula (8). There are no particular limitations on the solvent used in the present step, and an inert solvent that does not easily react with the reactants is preferable, examples of which include ethers such as tetrahydrofuran, diethyl ether, diisopropyl ether, dioxane or dimethoxyethane; halogenated hydrocarbons such as chloroform, carbon tetrachloride or 1,2-dichloroethane; hydrocarbons such as hexane or heptane; aromatic hydrocarbons such as benzene or toluene; acetic acid esters such as ethyl acetate or methyl acetate; amides such as N,N-dimethylformamide, N-methyl-2-piperidone or hexamethyl phosphorylamide; sulfoxides such as dimethylsulfoxide and mixtures thereof, with aromatic hydrocarbons being preferable and toluene, for example, being particularly preferable.

In the present step, the reaction proceeds under mild conditions by carrying out the reaction in the presence of pyridine and trifluoroacetic acid. Although the pyridine and trifluoroacetic acid used in the present step can be used in an equal amount to an excess amount with respect to the compound of formula (7), in consideration of ensuring that the reaction proceeds smoothly, purification treatment and the like, they are preferably used at 1.0 to 3.0 equivalents and 1.0 to 3.0 equivalents, respectively, and preferably at 1.0 to 2.0 equivalents and 1.0 to 2.0 equivalents, respectively.

The present step is composed of a total of two steps consisting of a step for introducing a phosphite group and an oxidation step, and although the diallyl-N,N-diisopropyl-phosphoramidate used in the step for introducing a phosphite group can be used in an equal amount to an excess amount with respect to the compound of formula (7), it is preferably used at 1.5 to 3.0 equivalents. The reaction time of the phosphite group introduction step is 0.5 to 24 hours and preferably 0.5 to 4 hours. The reaction temperature is −78° C. to room temperature and preferably −40 to 0° C. Although examples of the oxidant used in the oxidation step include hydrogen peroxide, m-chloroperbenzoic acid and oxone, hydrogen peroxide is most preferable. The reaction time of the oxidation step is 0.5 to 6 hours and preferably 1 to 3 hours. The reaction temperature is preferably −50 to 0° C.

The seventh step of the aforementioned production method consists of deprotecting 2-propenyl groups of the compound of formula (8) to produce the compound of formula (II). Removal of the 2-propenyl groups can be carried out by a method described in the references, such as hydrolysis using an acid or base, or a deallylation reaction using a metal catalyst such as a palladium catalyst. In particular, a deallylation reaction using a metal catalyst such as a palladium catalyst is preferable, while the use of a zero valence palladium catalyst, such as tetrakis(triphenylphosphine) palladium, is particularly preferable. Although a commercially available reagent can also be used for the zero valence palladium catalyst such as tetrakis(triphenylphosphine) palladium, a method in which the catalyst is generated within the reaction system is preferable in consideration of reagent stability, and for example, a combination of a divalent palladium reagent and a ligand such as triphenylphosphine is preferable. Examples of the divalent palladium catalyst used in the present step include palladium acetate, palladium chloride and bis(triphenylphosphine) palladium (II) chloride. For example, in the case of using palladium acetate for the divalent palladium reagent, although the palladium acetate can be used in a catalytic amount with respect to the compound of formula (8), in consideration of ensuring that the reaction proceeds smoothly, purification treatment and the like, it is preferably used at 0.01 to 0.50 equivalents and more preferably at 0.05 to 0.25 equivalents. The triphenylphosphine can be used at 1.5 to 10 equivalents with respect to the compound of formula (8), and more preferably used at 3.0 to 5.0 equivalents. A compound having an active methylene structure within a molecule thereof is preferable for the nucleophile used in the present reaction, and examples include linear organic acid esters such as ethyl cyanoacetate, cyclic organic acid esters such as Meldrum's acid (isopropylidene malonate), and cyclic ketones such as dimedone (5,5-dimethyl-1,3-cyclohexanedione), with cyclic organic acid esters such as Meldrum's acid and cyclic ketones such as dimedone being particularly preferable in terms of reduction of by-products.

The nucleophile used in the present step is used in an equal amount to an excess with respect to the palladium acetate, and preferably at 10 to 100 equivalents and more preferably at 20 to 30 equivalents. The reaction time is 1 to 12 hours and preferably 2 to 6 hours. The reaction temperature is 10 to 50° C. and preferably 20 to 40° C.

There are no particular limitations on the solvent used in the present step, and an inert solvent that does not easily react with the reactants is preferable, examples of which include ethers such as tetrahydrofuran, diethyl ether, diisopropyl ether, dioxane or dimethoxyethane; halogenated hydrocarbons such as chloroform, carbon tetrachloride or 1,2-dichloroethane; hydrocarbons such as hexane or heptane; aromatic hydrocarbons such as benzene or toluene, and mixtures thereof, with tetrahydrofuran being particularly preferable.

Although there are no particular limitations on the method used to remove residual palladium originating in the palladium catalyst used in the present step, a sulfur-containing compound such as trimercaptotriazine or sodium dimethyldithiocarbamate, a resin-immobilized adsorbent such as Daiaion (registered trademark) CR20 or column chromatography using, for example, a silica gel column is preferable, while a sulfur-containing compound such as trimercaptotriazine or sodium dimethyldithiocarbamate is preferable.

The eighth step of the aforementioned production method consists of adding a required amount of a sodium ion source to the compound represented by formula (II) to produce the compound represented by formula (IV).

There are no particular limitations on the sodium ion source used in the present step, and examples include a sodium-containing base such as sodium hydroxide or sodium carbonate, with sodium hydroxide being particularly preferable.

There are no particular limitations on the solvent used in the present step, and an inert solvent that does not easily react with the reactants is preferable, examples of which include alcohols such as methanol, ethanol, isopropanol or tert-butanol; ethers such as tetrahydrofuran, diethyl ether, diisopropyl ether, dioxane or dimethoxyethane; acetic acid esters such as ethyl acetate, methyl acetate or isopropyl acetate; ketones such as acetone or methyl ethyl ketone; nitrites such as acetonitrile; water and mixtures thereof, with alcohols such as methanol, ethanol, isopropanol or tert-butanol being preferable.

Since a compound represented by general formula (II) and a compound in the form of a tetrasodium salt represented by general formula (IV) antagonize gram-negative bacteremias having a high mortality rate caused by lipopolysaccharide components or endotoxins present in the outer membrane of gram-negative bacteria, and particularly lipid A, which plays a major role in endotoxic shock, and demonstrate superior anti-endotoxin activity while also demonstrating antagonistic activity against TLR4, which is one of the receptors that recognize bacterial cellular components, they are particularly useful as preventives or therapeutics for septicemia, endotoxemia or improving prognosis following coronary artery bypass surgery, and are preferable as active ingredients of pharmaceuticals.

However, the tetrasodium salt represented by general formula (IV) decomposes, although only slightly, during storage resulting in the formation of trace amounts of impurities over time. In the case of using a sodium salt of the compound represented by general formula (II) as a production raw material of a pharmaceutical, it is preferable to minimize the decomposition thereof over time and inhibit the formation of impurities.

Therefore, in the present invention, instead of using the tetrasodium salt represented by general formula (IV) as a sodium salt of the compound represented by general formula (II), a composition comprising a plurality of sodium salts is used that is represented by formula (I):

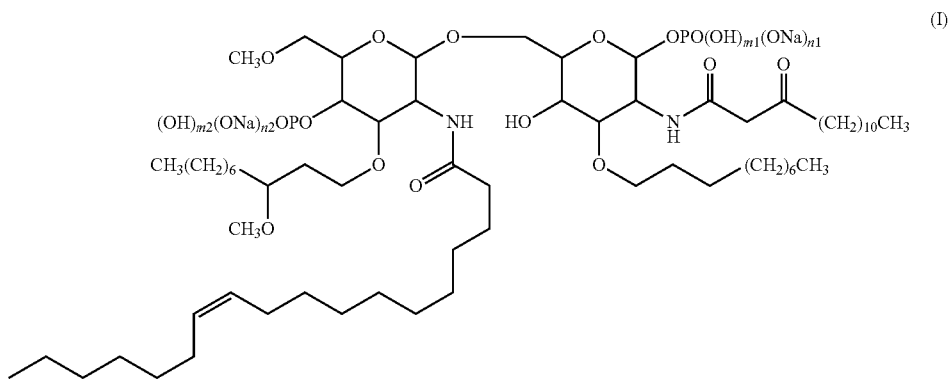

wherein, $m_1$, $n_1$, $m_2$ and $n_2$ respectively and independently represent a positive number between 0 and 2 of 0 or 2 or less, provided that $m_1+n_1=2$, $m_2+n_2=2$, $0<m_1+m_2<4$ and $0<n_1+n_2<4$. Since hydrogen atoms are present at a portion of the phosphoric acid sites of the sodium salts represented by formula (I), it can be said to be an acidic sodium salt of the compound represented by general formula (II). The sodium salts represented by formula (I) inhibits decomposition and formation of impurities over time as compared with the tetrasodium salt represented by general formula (IV).

In the aforementioned formula (I), $3 \leq n_1+n_2 < 4$ is preferable in terms of reducing formation of impurities, while $3.5 \leq n_1+n_2 \leq 3.8$ is more preferable.

In addition, the sodium content of the sodium salts represented by the aforementioned formula (I) is preferably within the range of 5.0 to less than 6.5% by weight, and more preferably 5.7 to 6.3% by weight, in terms of reducing formation of impurities.

The composition comprising a plurality of sodium salts represented by the aforementioned formula (I) can be prepared by incompletely neutralizing the compound represented by general formula (II) with a sodium-containing base. Here, "incompletely neutralizing" refers not to completely consuming (completely neutralizing) all of the hydrogen atoms at the phosphoric acid sites of the compound represented by general formula (II), but rather terminating neutralization in the state in which at least a portion of the phosphoric acid sites of the compound have hydrogen atoms. Thus, the sodium salts represented by general formula (III):

[CHEMICAL 13]

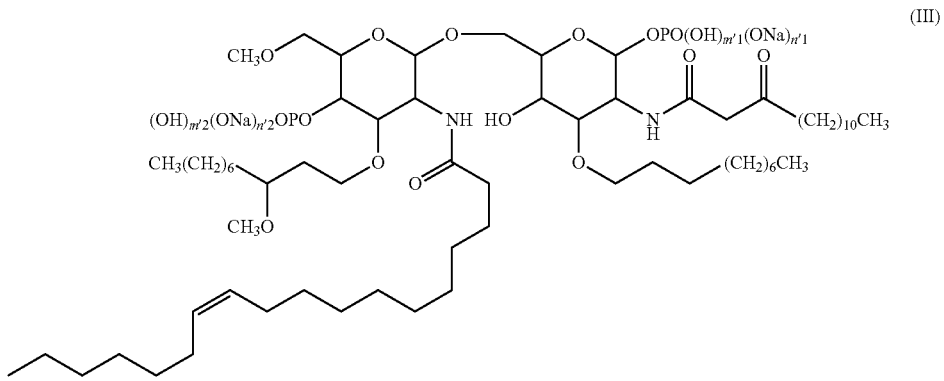

(wherein, $m'_1$, $n'_1$, $m'_2$ and $n'_2$ respectively and independently represent an integer of 0 or 2 or less, provided that $m'_1+n'_1=2$, $m'_2+n'_2=2$, $0<m'_1+m'_2<4$ and $0<n'_1+n'_2<4$) is present in the sodium salt represented by average formula (I) above.

There are no particular limitations on the sodium-containing base, and examples include sodium hydroxide, sodium carbonate and sodium bicarbonate, with sodium hydroxide being preferable. There are no particular limitations on the treatment temperature, and treatment can be carried out at, for example, 10 to 80° C. and preferably carried out at 20 to 40° C.

The aforementioned incomplete neutralization can be carried out in a suitable solvent. There are no particular limitations on the solvent used here, and examples include alcohols such as methanol, ethanol, isopropanol or tert-butanol; ethers such as tetrahydrofuran, diethyl ether, diisopropyl ether, dioxane or dimethoxyethane; acetic acid esters such as ethyl acetate, methyl acetate or isopropyl acetate; ketones such as acetone or methyl ethyl ketone; nitrites such as acetonitrile; water and mixtures thereof, with alcohols such as methanol, ethanol, isopropanol or tert-butanol being particularly preferable.

There are no particular limitations on the specific technique used for the aforementioned incomplete neutralization, and example of such a technique is method whereby a compound represented by general formula (II) is treated with less than 4 equivalents thereof of a monovalent sodium-containing base such as sodium hydroxide.

The sodium salt represented by the aforementioned average formula (I) is a mixture of various sodium salts. More specifically, the sodium salt represented by average formula (I) is a mixture of sodium salts represented by general formula (IV) and sodium salts represented by general formula (III), or in other words, the sodium salt represented by average formula (I) corresponds to that in which a portion of an aggregate comprised only of sodium salts represented by general formula (IV) is substituted with sodium salts represented by general formula (III).

Thus, another aspect of the present invention consists of a method for inhibiting decomposition of a sodium salt represented by general formula (IV) and inhibiting the formation of impurities within the salt represented by general formula (IV) by having the sodium salt represented by general formula (III).

Still another aspect of the present invention is a storage method enabling long-term storage by storing a sodium salt represented by general formula (IV) with a sodium salt represented by general formula (III). As a result, the present invention enables favorable storage for 1 month or more, preferably 3 months or more, and more preferably 6 months or more.

There are no particular limitations on the temperature at which the aforementioned method for inhibiting decomposition, method for inhibiting formation of impurities and storage method are carried out, and are preferably carried out at a comparatively low temperature to further inhibit decomposition and the formation of impurities, examples of which include 10 to 80° C., preferably 10 to 40° C. and more preferably 10 to 25° C.

A sodium salt represented by the aforementioned average formula (I) can be administered at a dosage effective for preventing or treating a target disease. The dosage can be, for example, 0.01 to 50 mg, preferably 0.05 to 25 mg and most preferably 1 to 12 mg per patient.

Although a pharmaceutical containing a sodium salt represented by the aforementioned average formula (I) can be administered by either oral or parenteral administration, it is preferably administered by a parenteral administration route. Parenteral administration routes include subcutaneous, intravenous, intramuscular and intraarterial infusion. The term "infusion" here is not limited to injection, but rather also includes administration through a catheter. Intravenous injection is the most preferable form of parenteral administration.

The aforementioned pharmaceutical can be in the form of, for example, granules, grains, powder, tablet, coated tablet, capsule or syrup in the case of oral administration, or in the form of, for example, an injection (such as intravenous injection, subcutaneous injection or intramuscular injection), suppository or externally applied preparation (such as transcutaneous preparation or ointment) in the case of parenteral administration.

An ordinarily used vehicle, binder, disintegration agent, lubricant, colorant, corrective, or as necessary, stabilizer, emulsifier, absorption promoter, surfactant, pH adjuster, preservative or antioxidant and the like can be incorporated in the various types of preparations described above.

EXAMPLES

Although the following provides a more detailed explanation of the present invention through examples thereof, the present invention is not limited to these examples.

Identification of the compounds as claimed in Reference Examples 1 to 7 was carried out by comparing retention times as determined by HPLC and using compounds synthesized in accordance with the production method described in WO 2004/074303 (Patent Document 3) as controls. Quantification of the compounds was carried out by calculating based on intensity obtained from a UV detector as determined by HPLC from a calibration curve generated by using compounds synthesized in accordance with the production method described in WO 2004/074303 (Patent Document 3) as controls.

There are no particular limitations on the stationary phase able to be used in HPLC, and a reverse phase column such as a C18 (ODS), C4, C8, C22 or C30 column is preferable. There are no particular limitations on the mobile phase, a solvent such as acetonitrile, methanol or water, or a mixed solvent thereof, is preferable, and favorable peak separation can be obtained by adding an acid such as perchloric acid, trifluoroacetic acid, acetic acid or phosphoric acid, or a salt thereof, or by adding an amine such as triethylamine or diethylamine. In addition, peak separation and retention time reproducibility are improved by maintaining the column at a constant temperature with a column oven and the like.

Reference Example 1

Synthesis of α-D-glucopyranose, (1Z)-1-propenyl 2-deoxy-3-O-[(3R)-3-methoxydecyl]-6-O-methyl-2-[[(11Z)-1-oxo-11-octadecenyl]amino]-, 4-(di-2-propenylphosphate)

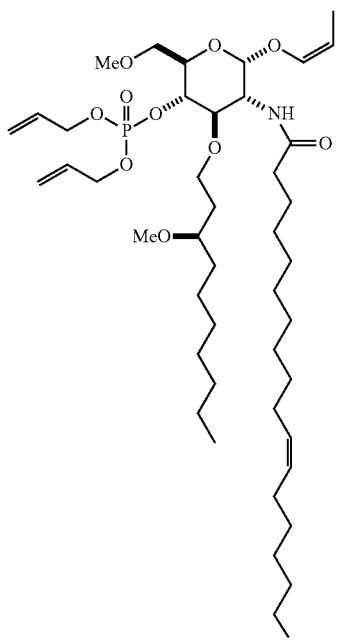

[CHEMICAL 14]

235 g of α-D-Glucose, (1Z)-1-propenyl 2-deoxy-3-O-[(3R)-3-methoxydecyl]-6-O-methyl-2-[[(11Z)-1-oxo-11-octadecenyl]amino]- [CAS registration no.: 748165-17-5] were dissolved in 933 mL of toluene in a 2 L 4-way flask followed by sequentially dropping in 129 mL of diallyl-N,N-diisopropylphosphoramidate, 39.4 mL of pyridine and 36.3 mL of trifluoroacetic acid at room temperature. 1.5 hours after completion of dropping, the reaction liquid was cooled to −20° C. and dilute acetonitrile solution (933 mL) containing 47.5 mL of hydrogen peroxide were was dropped in over the course of 37 minutes. Following completion of dropping, the reaction liquid was heated to 10° C. over the course of 40 minutes. Three hours later, the reaction liquid was quenched by adding 940 mL of 5% aqueous sodium bisulfite solution and then heated to room temperature. After extracting with ethyl acetate, the solution was refrigerated and used directly in the next reaction as a target compound solution.

Reference Example 2

Synthesis of α-D-Glucose, 2-Deoxy-3-O-[(3R)-3-methoxydecyl]-6-O-methyl-2-[[(11Z)-1-oxo-11-octadecenyl]amino]-, 4-(di-2-propenylphosphate)

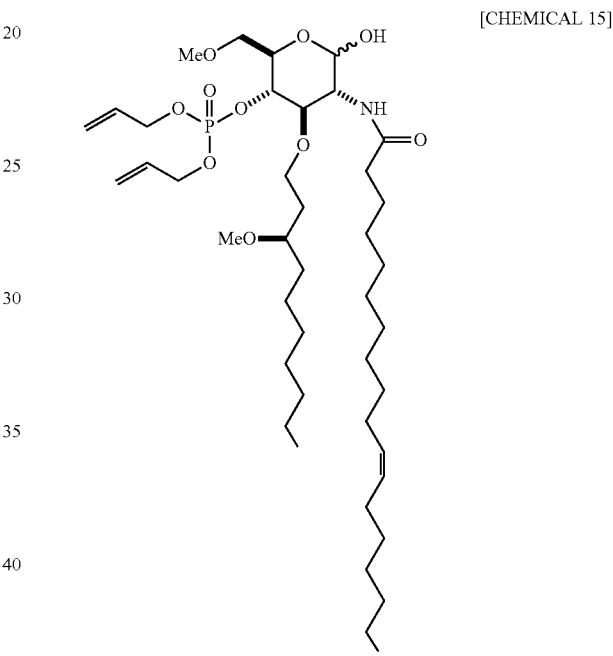

[CHEMICAL 15]

The α-D-glucopyranose, (1Z)-1-propenyl 2-deoxy-3-O-[(3R)-3-methoxydecyl]-6-O-methyl-2-[[(11Z)-1-oxo-11-octadecenyl]amino]-, 4-(di-2-propenylphosphate) solution obtained in Reference Example 1 was washed with 699 mL of 1 N aqueous hydrochloric acid followed by the addition of 27.9 mL of 5 N aqueous hydrochloric acid and stirring for 5 hours at room temperature. After neutralizing with 699 mL of 5% aqueous sodium bicarbonate, the solution was separated with ethyl acetate and the organic layer was washed with 699 mL of 5% saline solution. After drying by adding 69.9 g of anhydrous magnesium sulfate, the solution was filtered and the filtrate was concentrated under reduced pressure. 466 mL of acetone were added to the residue followed by again concentrating under reduced pressure. This acetone treatment was repeated to obtain 289.1 g of a crude form of the target compound (content: 92.1%, contained amount: 266.3 g). Yield: 97%.

1065 mL of acetonitrile were added to 289.1 g of the resulting crude form followed by stirring for 5 minutes at 20° C., cooling to 0° C. in 4 hours and then further stirring for 4 hours. The precipitated crystals were filtered out followed by drying overnight at room temperature under reduced pressure to obtain the target compound in an amount equivalent to 228.6 g.

Reference Example 3

Synthesis of α-D-glucopyranose, 2-deoxy-3-O-[(3R)-3-methoxydecyl]-6-O-methyl-2-[[(11Z)-1-oxo-11-octadecenyl]amino]-, 4-(di-2-propenylphosphate) 1-(2,2,2-trichlroethaneimidate)

[CHEMICAL 16]

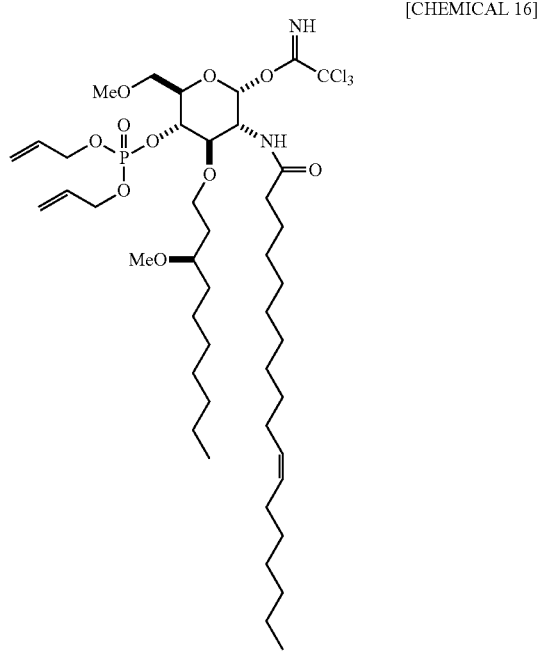

heptane to obtain 432 g of the target compound (content: 63.9%, containing 171.4 mL of heptane). Yield: 87.5%.

Reference Example 4

Synthesis of α-D-glucopyranoside, (1Z)-1-propenyl 6-O-[4-O-[bis(2-propenyloxy)phosphynyl]-2-deoxy-3-O-[(3R)-3-methoxydecyl]-6-O-methyl-2-[[(11Z)-1-oxo-11-octadecenyl)amino]-β-D-glucopyranosyl]-3-O-decyl-2-deoxy-2-[(1,3-dioxotetradecyl)amino]-, 4-(2-propenylcarbonate)

[CHEMICAL 17]

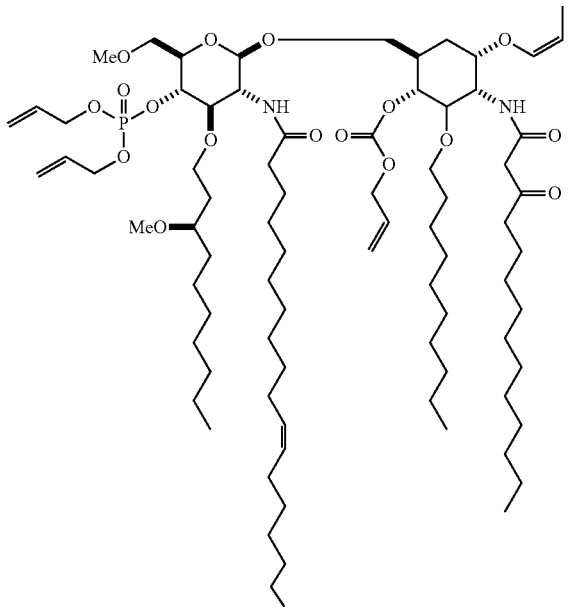

280 g of α-D-glucose, 2-deoxy-3-O-[(3R)-3-methoxydecyl]-6-O-methyl-2-[[(11Z)-1-oxo-11-octadecenyl]amino]-, 4-(di-2-propenylphosphate), 46.8 g of potassium carbonate, 560 mL of methyl acetate, 170 mL of trichloroacetonitrile and 8.4 mL of water were added to a 2 L 4-way flask followed by stirring for 2 hours at 0° C. in the presence of a nitrogen atmosphere. The reaction liquid was filtered with celite and concentrated under reduced pressure at 40° C. Continuing, the concentrate was co-boiled three times with 560 mL of A heptane solution of 410.8 g of α-D-glucopyranose, 2-deoxy-3-O-[(3R)-3-methoxydecyl]-6-O-methyl-2-[[(11Z)-1-oxo-11-octadecenyl]amino]-, 4-(di-2-propenylphosphate) 1-(2,2,2-trichloroethaneimidate) (content: 50.4%), 249.7 mL of heptane, 105.9 g of α-D-glucopyranoside, (1Z)-1-propenyl 3-O-decyl-2-deoxy-2-[(1,3-dioxotetradecyl)amino]-, 4-(2-propenylcarbonate) [CAS registration no.: 185955-29-7], 140 mL of toluene and 2.89 mL of methanesulfonic acid were sequentially added to a 2 L 4-way flask followed by stirring for 15 hours at 25° C. in the presence of a nitrogen atmosphere. The reaction liquid was extracted by adding 2000 mL of ethyl acetate and 1000 mL of water and following liquid separation, the organic layer was sequentially washed with 1000 mL of 5% aqueous sodium bicarbonate solution and 1000 mL of 10% saline solution. After concentrating under reduced pressure (bath temperature: 45 to 50° C.), 800 mL of methanol were added to the residue followed by repeating the same procedure to obtain a crude form of the target compound.

1920 mL of methanol were added to the resulting crude form and impurities were filtered out with celite. Insoluble matter and celite were washed with methanol. Moreover, after adding 1400 mL of methanol to the solution, the solution was cooled to 17° C. followed by dropping in 375 mL of water. Subsequently, the solution was cooled to −20° C. and stirred for 45 minutes followed by filtering. The filtered substance was washed with 400 mL of 90% aqueous ethanol solution pre-cooled to 0° C. followed by drying under reduced pressure using a Büchner funnel to obtain 427.2 g of a wet form.

427.2 g of the wet form were placed in a 10 L 4-way flask and dissolved by addition of 2400 mL of methanol. After cooling to 10° C., 180 mL of water were dropped in. Following completion of dropping, the solution was cooled to 0° C., stirred for 50 minutes and filtered. The filtered substance was washed with 400 mL of 90% aqueous methanol pre-cooled to 0° C. followed by drying under reduced pressure at 35° C. to obtain 199.5 g of the target compound (content: 92.2%). Yield: 92.6%.

Reference Example 5

Synthesis of α-D-glucopyranose, 6-O-[4-O-[bis(2-propenyloxy)phosphynyl]-2-deoxy-3-O-[(3R)-3-methoxydecyl]-6-O-methyl-2-[[(11Z)-1-oxo-11-octadecenyl)amino]-β-D-glucopyranosyl]-3-O-decyl-2-deoxy-2-[(1,3-dioxotetradecyl)amino]-, 4-(2-propenylcarbonate)

[CHEMICAL 18]

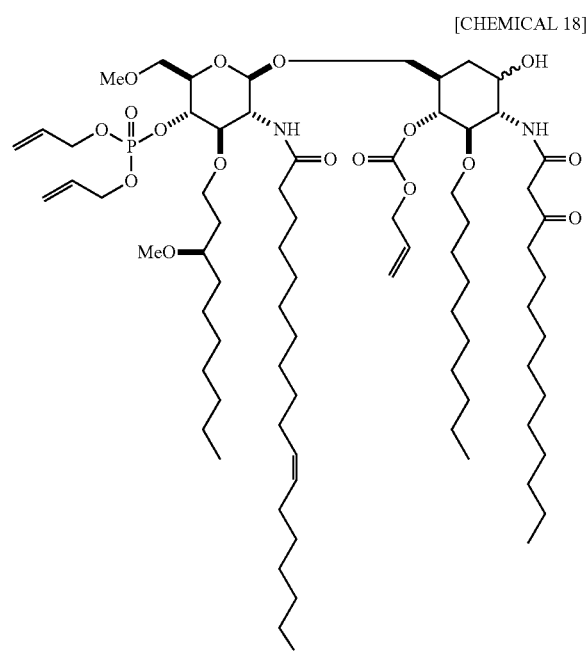

199.0 g of α-D-glucopyranoside, (1Z)-1-propenyl 6-O-[4-O-[bis(2-propenyloxy)phosphynyl]-2-deoxy-3-O-[(3R)-3-methoxydecyl]-6-O-methyl-2-[[(11Z)-1-oxo-11-octadecenyl)amino]-β-D-glucopyranosyl]-3-O-decyl-2-deoxy-2-[(1,3-dioxotetradecyl)amino]-, 4-(2-propenylcarbonate) (content: 92.2%), 1990 mL of acetonitrile and 34.6 mL of 1 N aqueous hydrochloric acid were added to a 4-way flask followed by stirring for 2 hours at a vacuum of 130 hPa and 30° C. Moreover, depressurization and jacket temperature were gradually increased, and acetonitrile was concentrated to about ¾ the original volume at a final vacuum of 106 hPa. The concentrate was extracted by adding 995 mL of 10% saline solution and 1493 mL of ethyl acetate. Subsequently, the organic layer was washed with 995 mL of 5% aqueous sodium bicarbonate solution and 995 mL of 10% saline solution in that order. The organic layer was dried with 60 g of anhydrous magnesium sulfate and then filtered. The filtrate was concentrated followed by dissolving by adding 640 ml of toluene to obtain 778.1 g of a toluene solution of the target compound (contained amount: equivalent to 155.6 g). Yield: 87.2%.

Reference Example 6

Synthesis of α-D-glucopyranose, 6-O-[4-O-[bis(2-propenyloxy)phosphynyl]-2-deoxy-3-O-[(3R)-3-methoxydecyl]-6-O-methyl-2-[[(11Z)-1-oxo-11-octadecenyl)amino]-β-D-glucopyranosyl]-3-O-decyl-2-deoxy-2-[(1,3-dioxotetradecyl)amino]-, 1-(di-2-propenylphosphate) 4-(2-propenylcarbonate)

[CHEMICAL 19]

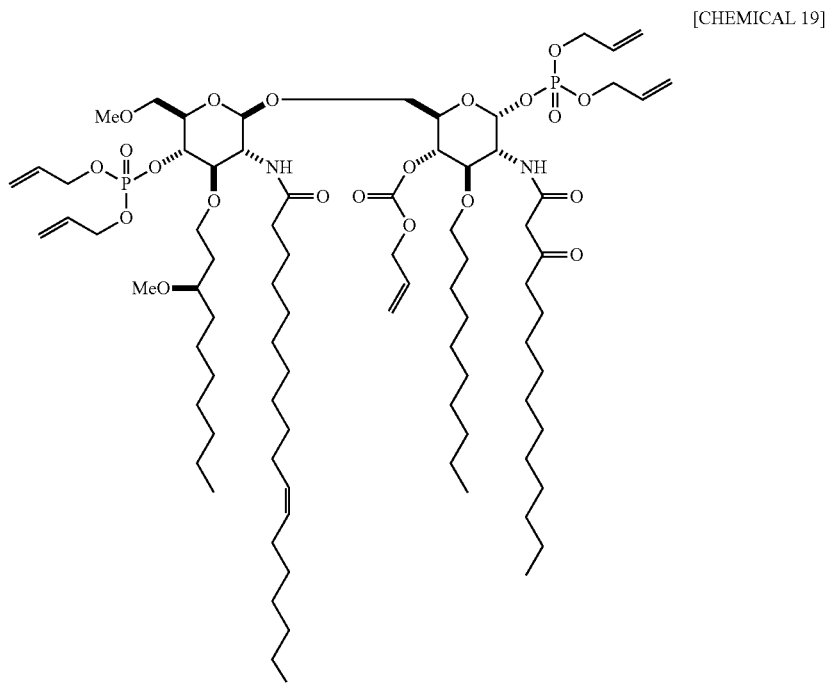

550.6 g of a toluene solution of α-D-glucopyranose, 6-O-[4-O-[bis(2-propenyloxy)phosphynyl]-2-deoxy-3-O-[(3R)-3-methoxydecyl]-6-O-methyl-2-[[(11Z)-1-oxo-11-octadecenyl]amino]-β-D-glucopyranosyl]-3-O-decyl-2-deoxy-2-[(1,3-dioxotetradecyl)amino]-, 4-(2-propenylcarbonate) (contained amount: equivalent to 110 g) was concentrated under reduced pressure at 50° C. A solution resulting from dissolving the residue by adding 440 mL of toluene was concentrated under reduced pressure at a bath temperature of 45 to 50° C. Moreover, after adding 440 mL of toluene, the atmosphere was replaced with nitrogen to obtain 537.6 g of a toluene solution (contained amount: 109.13 g). After concentrating this solution under reduced pressure, 665 mL of dry toluene were added followed by replacing the atmosphere with nitrogen. After adding 11.91 mL of trifluoroacetic acid and stirring for 15 hours, 12.50 mL of pyridine were added. After cooling to −20° C., 37.15 mL of N,N-diisopropylphosphoramidate were dropped in. Thirty minutes after completion of dropping, the solution was cooled to −30° C. followed by dropping in 15.17 mL of 30% hydrogen peroxide. Six minutes after completion of dropping, a constant temperature bath was set to −20° C. After 1 hour and 10 minutes, 655 mL of a 5% aqueous sodium thiosulfate solution were added to quench the reaction. After extracting by addition of 655 mL of ethyl acetate, and sequentially washing the organic layer with 655 mL of 0.5 N aqueous hydrochloric acid, 655 mL of 10% saline solution, 655 mL of 5% aqueous sodium bicarbonate solution and 655 mL of 10% saline solution, the washed organic layer was dried by addition of 43.7 g of anhydrous magnesium sulfate followed by filtering. The filtrate was concentrated under reduced pressure to obtain 159.0 g of the target compound (contained amount: 101.6 g). Yield: 83.5%.

Reference Example 7

Synthesis of α-D-glucopyranose, 3-O-decyl-2-deoxy-6-O-(2-deoxy-3-O-[(3R)-3-methoxydecyl]-6-O-methyl-2-[[(11Z)-1-oxo-11-octadecenyl]amino]-4-O-phosphono-β-D-glucopyranosyl]-2-[(1,3-dioxotetradecyl)amino]-1-(dihydrogen phoshate)

[CHEMICAL 20]

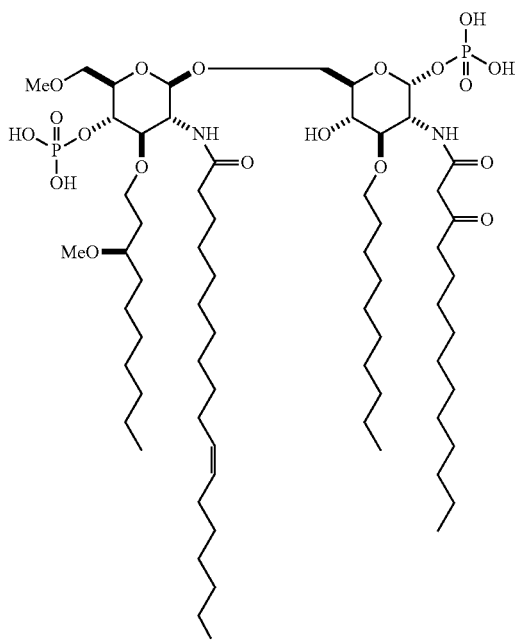

70.49 g of Meldrum's acid, 2.93 g of palladium acetate and 51.3 g of triphenylphosphine were placed in a 3 L 4-way flask. The atmosphere was replaced with nitrogen followed by the addition of 1321 mL of tetrahydrofuran. A tetrahydrofuran solution (203 mL) containing 101.6 g of α-D-glucopyranose, 6-O-[4-O-[bis(2-propenyloxy)phosphynyl]-2-deoxy-3-O-[(3R)-3-methoxydecyl]-6-O-methyl-2-[[(11Z)-1-oxo-11-octadecenyl]amino]-β-D-glucopyranosyl]-3-O-decyl-2-deoxy-2-[(1,3-dioxotetradecyl)amino]-, 1-(2-propenylphosphate) 4-(2-propenylcarbonate) were added followed by stirring for 2 hours at 32° C. and additionally stirring for 4 hours at 30° C. 250 mL of methanol were added to the reaction liquid followed by concentrating under reduced pressure to obtain 466.7 g of a residue. After adding 4570 mL of methanol thereto and dissolving by heating to 40° C., 5.55 g of trimercaptotriazine were added followed by stirring overnight at room temperature. The precipitated trimercaptotriazine-palladium complex was filtered out and washed with methanol to obtain 4330 g of a filtrate.

3908.2 mL of this methanol solution were concentrated under reduced pressure to obtain 440.9 g of a residue. 450 mL of acetone were added to the residue followed by concentrating under reduced pressure, again adding 450 mL of acetone and concentrating. After refrigerating the residue overnight, 1800 mL of acetone were added followed by heating to 40° C. and stirring for 1.5 hours. This was then allowed to cool in air followed by stirring for 1.5 hours at 30° C. or lower and filtering. After washing the filtered substance with 750 mL of acetone, the resulting solid was dried under reduced pressure at 35 to 40° C. to quantitatively obtain 104.48 g of a crude form in the form of a free acid form of the target compound (content: 74.2%).

[Column Purification]
1) Purification Using Hydrophobic Adsorption Resin Column

After dissolving 93.5 g of the aforementioned free acid form (free acid form content: 64.5%) in 10 L of methanol, 1110 mL of purified water were added and a portion of the unwanted substances were subjected to clarification filtration. The filtration residue was washed with 50 mL of 90% aqueous methanol followed by combining the washing and filtrate. The solution was applied to a hydrophobic adsorption resin column (load factor: 1% w/column volume, Sepabeads (registered trademark) SP20SS, Mitsubishi Chemical Corp.). The column was eluted with 90% aqueous methanol to purify the free acid form. The yield was 54.3 g (as determined by HPLC) as the free acid form (column yield: 90%).

2) Purification Using Anion Exchange Resin Column

Half of the main fraction of a hydrophobic adsorption resin column (Sepabeads (registered trademark), SP20SS) was applied to an anion exchange resin column (load factor: 0.5% w/column volume, Toyopearl (registered trademark), DEAE650M, Tosoh Corp.). After applying to the column, 95% aqueous methanol (mobile phase A) and 95% aqueous methanol (containing 0.25 mol/L sodium acetate) (mobile phase B) were passed through an anion exchange resin column (Toyopearl (registered trademark), DEAE650M) under gradient conditions to purify the free acid form. The same procedure was carried out on the remaining half to obtain a total of 48.3 g (as determined by HPLC) as the free acid form (column yield: 89%).

[Precipitation of Purified Substance]
17.6 L of acetonitrile were dropped into 11 L of the main fraction obtained during the aforementioned purification using an anion exchange resin column (48.3 g as free acid form) at 25° C. Following completion of dropping, stirring was continued for 2 hours and the precipitated precipitate was filtered under reduced pressure. When the filtered precipitate was dried under reduced pressure (bath temperature: 25° C.), the yield of the precipitate was 46.9 g. When HPLC quantitative analysis and measurement of sodium content to be described later were carried out on the resulting precipitate, the free acid form content was 89.5% (w/w), the amount of the free acid form was 42.0 g (yield: 87%) and the sodium content was 4.80% (w/w) (as the anhydrous basis).

Example 1

39.0 g of a precipitate from the main fraction of a DEAE column (free acid form content: 34.5 g) and 942.8 L of methanol were placed in a 3 L 4-way flask followed by stirring at 25° C. 127.3 mL of 0.2 N a sodium hydroxide-methanol solution were added to the 3 L 4-way flask followed by stirring overnight. The solution was filtered to clarity and the filtrate was transferred to a 10 L 4-way flask. 3413 mL of acetone at 25° C. were dropped into the 10 L 4-way flask to which the filtrate had been transferred. The precipitated precipitate was filtered out and dried under reduced pressure at 25° C. to obtain the aforementioned sodium salt. The yield was 37.0 g, the content of the free acid form was 89.46% (w/w) and the amount of the free acid form was 33.1 g (yield: 95.9%).

[Measurement of Sodium Content]

The sodium content of the salt obtained in Example 1 was measured in the manner described below. 25±2.5 mg of sample (precipitate) were accurately weighed out and placed in a 50 mL conical tube followed by completely dissolving by addition of 5 mL of methanol. 20 mL of an aqueous solution containing 2.5 mmol/L of oxalic acid were added to the resulting solution to prepare a sample solution by stirring to homogeneity (n=2). On the other hand, the same procedure was carried out to prepare a blank solution ($BL_{smp.}$) for the sample solution (n=1).

A mixed solution of 2.5 mmol/L aqueous oxalic acid and methanol (80:20, v/v) were added to 3 mL of sodium ion standard solution (1000 mg/L) and brought to a final volume of 50 mL for use as a sodium standard solution (n=1). On the other hand, the same procedure was carried out to prepare a blank solution ($BL_{std.}$) for the sodium standard solution (n=1).

10 μL each of the sample solutions, sodium standard solution and blank solutions were injected at a rate of 1.0 mL/min (mobile phase: 2.5 mmol/L aqueous oxalic acid solution) with the column temperature set at 40° C. to determine the areas of the sodium ion peaks using an ion chromatography (IC) system equipped with an electric conductivity detector, an analytical column (consisting of silica gel having a diameter of about 7 μm bonded to cation exchange groups in the form of carboxyl groups packed into a tube having an inner diameter of 4.6 mm and length of 10 cm: e.g., SHIM-PACK IC-C3, Shimadzu Corp.), a guard column 1 (consisting of triacontyl-silylated silica gel having a diameter of about 20 μm packed into a tube having an inner diameter of 6.0 mm and length of 5 cm: e.g., ERP20, Develosil Ltd.) and a guard column 2 (consisting of the same particles as the analytical column packed into a tube having an inner diameter of 4.6 mm and length of 7.5 mm: e.g., SHIM-PACK IC-GC3 II, Shimadzu Corp.). Sodium content was determined according to the following formulas from the areas of the sodium ion peaks.

Sodium ion content (%) (as is) = [FORMULA 1]

$$\frac{(A_{smp.} - A_{BLsmp.})}{(A_{std.} - A_{BLstd.})} \times \frac{f}{W_{smp.}} \times \frac{3}{20}$$

Sodium ion content (%) (as anhydrous basis) =

$$\text{Sodium ion content (\%) (as is)} \times \frac{100}{(100 - KF_{smp.})}$$

$A_{smp.}$: Sodium ion peak area in sample solution (avg. of n=2)

$A_{BLsmp.}$: Sodium ion peak area in blank solution ($BL_{smp.}$) for sample solution (avg. of n=2)

$A_{std.}$: Sodium ion peak area in sodium standard solution (avg. of n=2)

$A_{BLstd.}$: Sodium ion peak area in blank solution ($BL_{std.}$) for sodium standard solution (avg. of n=2)

f: Assayed value indicated for sodium ion standard solution (indicated in mg/L)

$W_{smp.}$: Weighed amount of sample (mg)

$KF_{smp.}$: Moisture content of sample (%)

As result, since the sodium content (anhydrous basis) of the salt obtained in Example 1 is 6.09% by weight, the molecular weight of the free acid form is 1313.68, the atomic weight of sodium is 23.00 and the atomic weight of hydrogen is 1.01, the salt was determined to be a 3.70 Na salt ($n_1+n_2$=3.70 in average formula (I)) from 1313.68×6.09/(2300−21.99× 6.09)= 3.70.

Example 2

A salt having a sodium content (anhydrous basis) of 4.75% by weight (2.84 Na salt) was obtained by carrying out the aforementioned procedure through precipitation of the purified substance.

Example 3

A salt having a sodium content (anhydrous basis) of 6.05% by weight (3.67 Na salt) was obtained by carrying out the same procedure as Example 1 using 6.0 g of DEAE main fraction precipitate, 74.5 mL of methanol for dissolving, 15.2 mL of 0.2 N sodium hydroxide-methanol solution and 270 mL of acetone.

Example 4

A salt having a sodium content (anhydrous basis) of 6.45% by weight (3.93 Na salt) was obtained by carrying out the same procedure as Example 1 using 1.84 g of DEAE main fraction precipitate, 21.4 mL of methanol for dissolving, 6.3 mL of 0.2 N sodium hydroxide-methanol solution and 83 mL of acetone.

Comparative Example 1

A salt having a sodium content (anhydrous basis) of 6.65% by weight (4.06 Na salt) was obtained by carrying out the same procedure as Example 1 using 2.47 g of DEAE main fraction precipitate, 35.4 mL of methanol for dissolving, 8.7 mL of 0.2 N sodium hydroxide-methanol solution and 111 mL of acetone.

[Storage Stability Test]

The salts of Examples 2 to 4 and Comparative Example 1 were placed in a screw-cap glass bottle and stored for 30 days at 25° C. followed by determination of formation rates of impurities A, B and C as described below.

Each salt of Examples 2 to 4 and Comparative Example 1 was dissolved in methanol to prepare a solution having a concentration of 5 mg/mL. When HPLC analysis was carried out under the conditions indicated in Table 1 below on each solution and a blank solution (methanol only), three types of decomposition products were confirmed. Consequently, formation rates (converted to monthly rates) were calculated for each of the three types of decomposition products (impurities A, B and C) using the area percent.

TABLE 1

| Column | YMC Carotenoid, C-30, 250 × 4.6 mm, 5 μm | | |
|---|---|---|---|
| Column temperature | 35° C. | | |
| Flow rate | 1.0 mL/min | | |
| | Time | Liquid A (%) | Liquid B (%) |
| Gradient | 0 min | 100 | 0 |
| | 15 min | 100 | 0 |
| | 35 min | 0 | 100 |
| | 40 min | 0 | 100 |
| Injection volume | 25 μL | | |
| Detection | UV 254 nm and 208 nm | | |

Liquid A: Obtained by mixing 980 mL of methanol and 20 mL of phosphoric acid and degassing.
Liquid B: Obtained by mixing 500 mL of methanol and 500 mL of dichloromethane, removing 980 mL of that mixture and mixing with 20 mL of phosphoric acid followed by degassing.

The results are shown in Tables 2 to 5.

TABLE 2

| Impurity A Days | 2.84 Na Salt | 3.67 Na Salt | 3.93 Na Salt | 4.06 Na Salt |
|---|---|---|---|---|
| 0 | 0.00 | 0.00 | 0.00 | 0.00 |
| 1.0 | — | 0.00 | 0.03 | 0.06 |
| 1.9 | — | 0.01 | 0.04 | 0.08 |
| 4.5 | — | 0.01 | 0.06 | 0.12 |
| 18 | 0.00 | — | — | — |
| Formation rate (%/month) | 0.00 | 0.072 | 0.363 | 0.729 |

TABLE 3

| Impurity B Days | 2.84 Na Salt | 3.67 Na Salt | 3.93 Na Salt | 4.06 Na Salt |
|---|---|---|---|---|
| 0 | 0.00 | 0.08 | 0.14 | 0.18 |
| 1.0 | — | 0.12 | 0.26 | 0.36 |
| 1.9 | — | 0.09 | 0.29 | 0.48 |
| 4.5 | — | 0.13 | 0.38 | 0.67 |
| 18 | 0.00 | — | — | — |
| Formation rate (%/month) | 0.00 | 0.267 | 1.455 | 3.117 |

TABLE 4

| Impurity C Days | 2.84 Na Salt | 3.67 Na Salt | 3.93 Na Salt | 4.06 Na Salt |
|---|---|---|---|---|
| 0 | 0.00 | 0.00 | 0.00 | 0.00 |
| 1.0 | — | 0.00 | 0.00 | 0.00 |
| 1.9 | — | 0.00 | 0.00 | 0.00 |
| 4.5 | — | 0.01 | 0.01 | 0.00 |
| 8.8 | — | 0.01 | 0.01 | 0.00 |
| 18 | 0.17 | — | — | — |
| 29.5 | — | 0.07 | 0.06 | 0.03 |
| Formation rate (%/month) | 0.282 | 0.072 | 0.063 | 0.033 |

TABLE 5

| | | | Impurity A | Impurity B | Impurity C |
|---|---|---|---|---|---|
| Impurity Formation Rate | Example 2 | 2.84 Na salt (Na content: 4.75 wt %) | 0.000 | 0.000 | 0.282 |
| | Example 3 | 3.67 Na salt (Na content: 6.05 wt %) | 0.072 | 0.267 | 0.072 |
| | Example 4 | 3.93 Na salt (Na content: 6.45 wt %) | 0.363 | 1.455 | 0.063 |
| | Comparative Example 1 | 4.06 Na salt (Na content: 6.65 wt %) | 0.729 | 3.117 | 0.033 |

Figure 2:
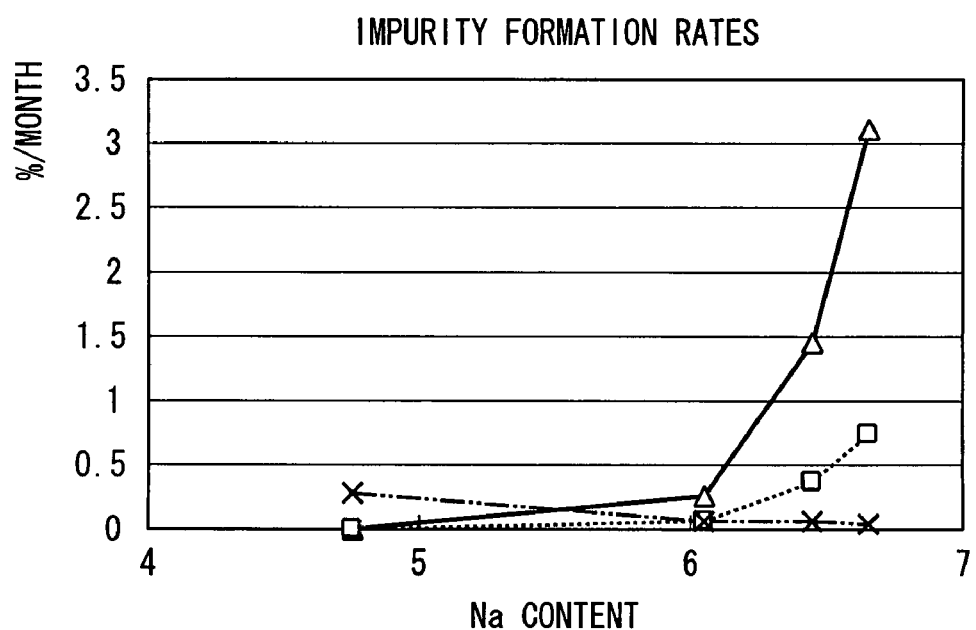

The results of Table 5 are shown in FIGS. 1 and 2. In FIG. 1, the values of $n_1+n_2$ of the salts of Examples 2 to 4 and Comparative Example 1 are plotted on the horizontal axis, while in FIG. 2, the values plotted on the horizontal axis correspond to the sodium contents of the salts of Examples 2 to 4 and Comparative Example 1. It can be understood from FIG. 1 that the impurity formation rates of Examples 2 to 4 in which $n_1+n_2<4$ are lower than that of Comparative Example 1 in which $n_1+n_2=4$. A range of $3 \leq n_1+n_2<4$, and particularly a range of $3.5 \leq n_1+n_2 \leq 3.8$, results in even lower impurity formation rates. It can be similarly understood from FIG. 2 as well that the impurity formation rates of Examples 2 to 4 in which the sodium contents are less than 6.65% by weight are lower than that of Comparative Example 1 in which the sodium content is 6.65% by weight. A range of 5.0 to less than 6.5% by weight, and particularly a range of 5.7 to 6.3% by weight, results in even lower impurity formation rates.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A composition comprising a plurality of sodium salts represented by formula (I):

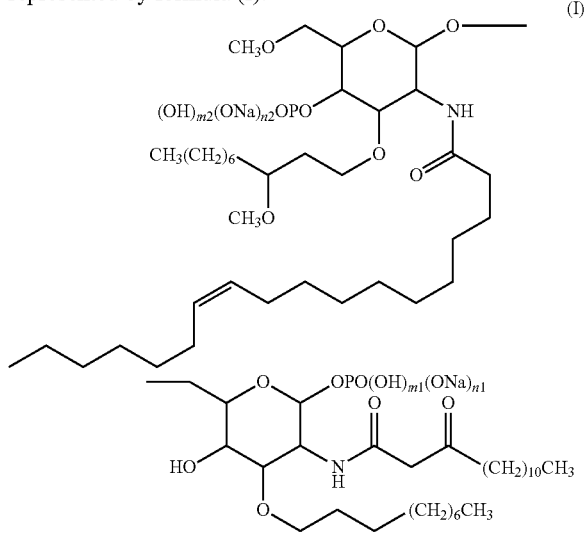

wherein, $m_1$, $n_1$, $m_2$ and $n_2$ respectively and independently represent a positive number between 0 and 2, provided that $m_1+n_1=2$, $m_2+n_2=2$, $0<m_1+m_2<4$ and $3.5 \leq n_1+n_2 \leq 3.8$.

2. The composition according to claim 1, wherein sodium content is 5.0 to less than 6.5% by weight.

3. The composition according to claim 1, wherein sodium content is 5.7 to 6.3% by weight.

4. A composition according to claim 1, wherein the composition inhibits the formation of impurities.

5. A composition according to claim 1, wherein the impurity formation rate of the composition is less than 3.879% per month.

6. A method for producing the composition according to any of claim 1, 2 or 3 comprising: incompletely neutralizing a composition comprising a compound represented by general formula (II):

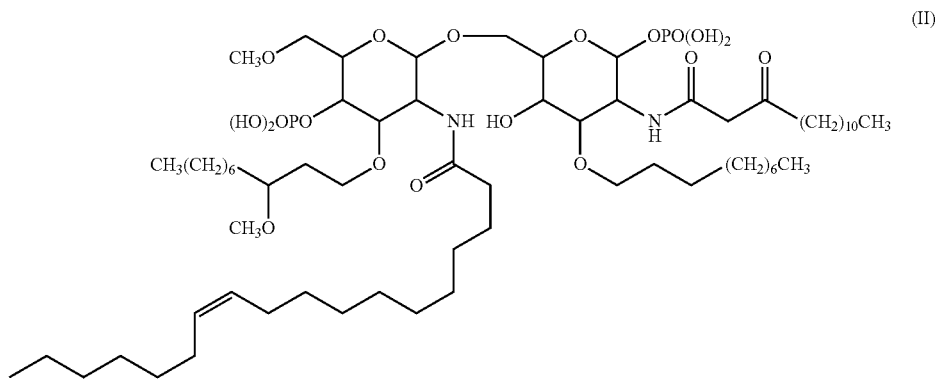

with a sodium-containing base.

* * * * *

UNITED STATES PATENT AND TRADEMARK OFFICE
CERTIFICATE OF CORRECTION

PATENT NO. : 8,207,144 B2  
APPLICATION NO. : 11/984770  
DATED : June 26, 2012  
INVENTOR(S) : Shin Sakurai et al.

Page 1 of 1

It is certified that error appears in the above-identified patent and that said Letters Patent is hereby corrected as shown below:

On the Title page, first column, Foreign Application Priority Data should read:

Item (30)    Foreign Application Priority Data

November 22, 2006 (JP)    2006-315020

Signed and Sealed this  
Eleventh Day of December, 2012

David J. Kappos  
*Director of the United States Patent and Trademark Office*